US007537932B1

(12) United States Patent
Hannum et al.

(10) Patent No.: US 7,537,932 B1
(45) Date of Patent: May 26, 2009

(54) ANTIBODIES THAT BIND PURIFIED MAMMALIAN FLT3 LIGANDS

(75) Inventors: Charles H. Hannum, Sunnyvale, CA (US); Janice A. Culpepper, Mountain View, CA (US); Frank D. Lee, Palo Alto, CA (US); Daniel Birnbaum, Marseille (FR)

(73) Assignees: Schering Corporation, Kenilworth, NJ (US); Inserm, Paris (FR)

( * ) Notice: Subject to any disclaimer, the term of this patent is extended or adjusted under 35 U.S.C. 154(b) by 0 days.

(21) Appl. No.: 08/472,168

(22) Filed: Jun. 7, 1995

Related U.S. Application Data

(60) Division of application No. 08/261,553, filed on Jun. 17, 1994, now abandoned, which is a continuation-in-part of application No. 08/162,413, filed on Dec. 3, 1993, now abandoned, which is a continuation-in-part of application No. 08/155,111, filed on Nov. 19, 1993, now abandoned, which is a continuation-in-part of application No. 08/112,391, filed on Aug. 24, 1993, now abandoned, which is a continuation-in-part of application No. 08/106,340, filed on Aug. 13, 1993, now abandoned, which is a continuation-in-part of application No. 08/092,549, filed on Jul. 16, 1993, now abandoned, which is a continuation-in-part of application No. 08/089,263, filed on Jul. 7, 1993, now abandoned, which is a continuation-in-part of application No. 08/065,231, filed on May 19, 1993, now abandoned.

(51) Int. Cl.
*C07K 16/24* (2006.01)

(52) U.S. Cl. ............... 435/335; 530/388.21; 530/387.9; 530/388.23

(58) Field of Classification Search ........... 530/387, 530/388; 424/130.1, 133.1, 134.1, 139.1, 424/141.1, 143.1, 145.1
See application file for complete search history.

(56) References Cited

U.S. PATENT DOCUMENTS

| 5,116,964 | A | 5/1992 | Capon | 536/27 |
| 5,185,438 | A | 2/1993 | Lemischka | 536/23.2 |
| 5,554,512 | A | 9/1996 | Lyman et al. | 435/69.5 |

FOREIGN PATENT DOCUMENTS

| EP | 0354808 | 2/1990 |
| WO | WO 92/17486 | 10/1992 |

OTHER PUBLICATIONS

A Leutz, et al., "Chicken Myelomoncytic Growth Factor," A. Habenicht, ed., Springer-Verlag, N.Y. 1990.
Abstracts 73-78, 570, 1668, 1677-1682, 1960, 1984-1986 from "Blood: Journal of the American Society of Hematology," vol. 86, No. 10, Supplement 1 to Nov. 15, 1995, American Society of Hematology 37th Annual Meeting, Dec. 1-5, 1995, Seattle WA.
Benoit Chabot, et al., "The Proto-Oncogene *c-kit* Encoding a Transmembrane Tyrosine Kinase Receptor Maps to the Mouse *W* Locus," *Nature*, vol. 335, pp. 88-89, Sep. 1988.
John G. Flanagan, et al., "The *kit* Ligand: A Cell Surface Molecule Altered in Steel Mutant Fibroblasts," *Cell* vol. 63, pp. 185-194, Oct. 1990.
Edwin N. Geissler, et al., "The Dominant-White Spotting (*W*) Locus of the Mouse Encodes the *c-kit* Proto-Oncogene," *Cell*, vol. 55, pp. 185-192, Oct. 1988.
William Matthews, et al., "A Receptor Tyrosine Kinase Specific to Hematopoietic Stem and Progenitor Cell-Enriched Populations," *Cell*, vol. 65, pp. 1143-1152, Jun. 1991.
Catherine J. McMahan, et al., "A Novel IL-1 Receptor, Cloned from B Cells by Mammalian Expression, Is Expressed in Many Cell Types," *EMBO J.*, vol. 10, No. 10, pp. 2821-2832, 1991.
Tony Pawson, et al., "Receptor Tyrosine Kinases: Genetic Evidence for Their Role in *Drosophila* and Mouse Development," *Trends in Genetics*, vol. 6, No. 11, pp. 350-356, Nov. 1990.
Olivier Rosnet, et al., "Murine Flt3, a Gene Encoding a Novel Tyrosine Kinase Receptor of the PDGFR/CSF1R Family," *Oncogene*, vol. 6, pp. 1641-1650, 1991.
C. Hannum et al., "Ligand for FLT3/FLK2 Receptor Tyrosine Kinase Regulates Growth of Haematopoietic Stem Cells and is Encoded by Variant RNAs," *Nature* 368:643-648, Apr. 14, 1994.
Stewart D. Lyman et al., "Cloning of the Human Homologue of the Murine flt3 Ligand: A Growth Factor for Early Hematopoietic Progenitor Cells," *Blood* 83:2795-2801, May 15, 1994.
Stewart D. Lyman et al., "Molecular Cloning of a Ligand for the flt3/flk-2 Tyrosine Kinase Receptor: A Proliferative Factor for Primitive Hematopoietic Cells," *Cell* 75:1157-1167, Dec. 17, 1993.

*Primary Examiner*—Lorraine Spector
(74) *Attorney, Agent, or Firm*—Schering-Plough Patent Dept.

(57) ABSTRACT

Flt3 ligand from a mammal, reagents related thereto including purified proteins, specific antibodies, and nucleic acids encoding said ligand. Methods of using said reagents and diagnostic kits are also provided.

21 Claims, 3 Drawing Sheets

```
                           SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
           (A) LENGTH: 11 amino acids
           (B) TYPE: amino acid
           (D) TOPOLOGY: linear (ii) MOLECULE TYPE: peptide (xi) SEQUENCE DESCRIPTION: SEQ ID NO:1:

Phe Val Gln Thr Xaa Ile Ser His Leu Leu Lys
   1               5                   10

(2) INFORMATION FOR SEQ ID NO:2:

(i) SEQUENCE CHARACTERISTICS:
           (A) LENGTH: 14 amino acids
           (B) TYPE: amino acid
           (D) TOPOLOGY: linear (ii) MOLECULE TYPE: peptide (xi) SEQUENCE DESCRIPTION: SEQ ID NO:2:

Asp Tyr Pro Val Thr Val Ala Val Asn Leu Gln Asp Glu Lys
   1               5                   10

(2) INFORMATION FOR SEQ ID NO:3:

(i) SEQUENCE CHARACTERISTICS:
           (A) LENGTH: 16 amino acids
           (B) TYPE: amino acid
           (D) TOPOLOGY: linear (ii) MOLECULE TYPE: peptide (xi) SEQUENCE DESCRIPTION: SEQ ID NO:3:

Thr Pro Asp Xaa Tyr Phe Ser His Ser Pro Ile Ser Ser Asn Phe Lys
   1               5                   10                  15

(2) INFORMATION FOR SEQ ID NO:4:

(i) SEQUENCE CHARACTERISTICS:
           (A) LENGTH: 10 amino acids
           (B) TYPE: amino acid
           (D) TOPOLOGY: linear (ii) MOLECULE TYPE: peptide (xi) SEQUENCE DESCRIPTION: SEQ ID NO:4:

Trp Ile Glu Gln Leu Lys Gln Pro Gly Ser
```

-continued

```
1               5               10
```

(2) INFORMATION FOR SEQ ID NO:5:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:5:

```
Glu Leu Thr Val His Leu Leu Lys
1               5
```

(2) INFORMATION FOR SEQ ID NO:6:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:6:

```
Ile Leu Phe Xaa Leu Phe Leu Gln Tyr Arg
1               5                   10
```

(2) INFORMATION FOR SEQ ID NO:7:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:7:

```
Ser His Ser Pro Ile Ser Ser Asn Phe
1               5
```

(2) INFORMATION FOR SEQ ID NO:8:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:8:

```
Trp Ile Glu Gln Leu Lys
1               5
```

(2) INFORMATION FOR SEQ ID NO:9:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:9:

```
Asp Tyr Pro Val Thr Val Ala Val Asn Leu Gln
1               5                   10
```

(2) INFORMATION FOR SEQ ID NO:10:

```
    (i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:10:

Asp Ala Tyr Phe Ser His Ser Pro Ile Ser Ser Asn Phe Lys Val Lys
1               5                   10                  15

Phe Arg Glu Leu Thr Val
            20

(2) INFORMATION FOR SEQ ID NO:11:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:11:

Asp Tyr Pro Val Thr Val Ala Ala
1               5

(2) INFORMATION FOR SEQ ID NO:12:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:12:

Thr Pro Asp Ala Tyr Phe Ser His Ser Pro Ile Ser Ser Asn Phe Lys
1               5                   10                  15

Val Lys Phe Arg Glu Leu Thr Val His Leu Leu Lys
            20                  25

(2) INFORMATION FOR SEQ ID NO:13:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:13:

Trp Ile Glu Gln Leu Lys
1               5

(2) INFORMATION FOR SEQ ID NO:14:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:14:

Phe Val Gln Thr Xaa Ile Ser His Leu Leu Lys
1               5                   10
```

(2) INFORMATION FOR SEQ ID NO:15:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:15:

```
Ile Leu Phe Xaa Leu Phe Ala Gln Tyr Arg
 1               5                  10
```

(2) INFORMATION FOR SEQ ID NO:16:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:16:

```
Asp Tyr Pro Val Thr Val Ala Val Asn Leu Gln
 1               5                  10
```

(2) INFORMATION FOR SEQ ID NO:17:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (xi) SEQUENCE DESCRIPTION: SEQ ID NO:17:

```
Thr Pro Asp Cys Tyr Phe Ser His Ser Pro Ile Ser Ser Asn Phe Lys
 1               5                  10                  15

Val Lys Phe Arg Glu Leu Thr Val His Leu Leu Lys Asp Tyr Pro Val
                20                  25                  30

Thr Val Ala Val Asn Leu Gln Asp Glu Lys
            35                  40
```

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
TTYGTNCARA CNAAYATH                                              18
```

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

TTYGTNCARA CNTGYATH 18

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

TTYGTNCARA CNAGYATH 18

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TTYGTNCARA CNTCNATH 18

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TTYGTNCARA CNACNATH 18

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GAYTAYCCNG TNACNGTN 18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

ACNCCNGAYA TNTAYTTY 18

(2) INFORMATION FOR SEQ ID NO:25:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:25:

TGGATHGARC ARCTNAAR                                          18

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

TGGATHGARC ARTTRAAR                                          18

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

AAYTTYAARG TNAARTTY                                          18

(2) INFORMATION FOR SEQ ID NO:28:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

ACTCCTGACT GTTACTTCAG CCACAGTCCC ATCTCCTCCA ACTTCAAAGT GAAGTTTAGA    60

GAGTTGACTG ACCACCTGCT TAAAGAT                                       87

(2) INFORMATION FOR SEQ ID NO:29:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GGATCCCGGG TACCTTCTAG AATTCCGGAG CGGCCGCTGC AGATCTCATC ACCATCACCA    60

TCACGATTAC AAGGACGATG ACGATAAGTA ATGA                               94

(2) INFORMATION FOR SEQ ID NO:30:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Asp Pro Gly Tyr Leu Leu Glu Phe Arg Ser Gly Arg Cys Arg Ser His
1               5                   10                  15

His His His His His Asp Tyr Lys Asp Asp Asp Lys
                20                  25

(2) INFORMATION FOR SEQ ID NO:31:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..303

(xi) SEQUENCE DESCRIPTION: SEQ ID NO:31:

```
ACT CCT GAC TGT TAC TTC AGC CAC AGT CCC ATC TCC TCC AAC TTC AAA        48
Thr Pro Asp Cys Tyr Phe Ser His Ser Pro Ile Ser Ser Asn Phe Lys
1               5                   10                  15

GTG AAG TTT AGA GAG TTG ACT GAC CAC CTG CTT AAA GAT TAC CCA GTC        96
Val Lys Phe Arg Glu Leu Thr Asp His Leu Leu Lys Asp Tyr Pro Val
                20                  25                  30

ACT GTG GCC GTC AAT CTT CAG GAC GAG AAG CAC TGC AAG GCC TTG TGG       144
Thr Val Ala Val Asn Leu Gln Asp Glu Lys His Cys Lys Ala Leu Trp
            35                  40                  45

AGC CTC TTC CTA GCC CAG CGC TGG ATA GAG CAA CTG AAG ACT GTG GCA       192
Ser Leu Phe Leu Ala Gln Arg Trp Ile Glu Gln Leu Lys Thr Val Ala
        50                  55                  60

GGG TCT AAG ATG CAA ACG CTT CTG GAG GAC GTC AAC ACC GAG ATA CAT       240
Gly Ser Lys Met Gln Thr Leu Leu Glu Asp Val Asn Thr Glu Ile His
65                  70                  75                  80

TTT GTC ACC TCA TGT ACC TTC CAG CCC CTA CCA GAA TGT CTG CGA TTC       288
Phe Val Thr Ser Cys Thr Phe Gln Pro Leu Pro Glu Cys Leu Arg Phe
                85                  90                  95

GTA CAG ACC AAT ATA                                                   303
Val Gln Thr Asn Ile
            100
```

(2) INFORMATION FOR SEQ ID NO:32:

(i) SEQUENCE CHARACTERISTICS:
        (A) LENGTH: 101 amino acids
        (B) TYPE: amino acid
        (D) TOPOLOGY: linear (ii) MOLECULE TYPE: protein (xi) SEQUENCE DESCRIPTION: SEQ ID NO:32:

Thr Pro Asp Cys Tyr Phe Ser His Ser Pro Ile Ser Ser Asn Phe Lys
1               5                   10                  15

Val Lys Phe Arg Glu Leu Thr Asp His Leu Leu Lys Asp Tyr Pro Val
                20                  25                  30

```
Thr Val Ala Val Asn Leu Gln Asp Glu Lys His Cys Lys Ala Leu Trp
         35                  40                  45

Ser Leu Phe Leu Ala Gln Arg Trp Ile Glu Gln Leu Lys Thr Val Ala
     50                  55                  60

Gly Ser Lys Met Gln Thr Leu Leu Glu Asp Val Asn Thr Glu Ile His
 65              70                  75                      80

Phe Val Thr Ser Cys Thr Phe Gln Pro Leu Pro Glu Cys Leu Arg Phe
                 85                  90                  95

Val Gln Thr Asn Ile
             100

(2) INFORMATION FOR SEQ ID NO:33:

(i) SEQUENCE CHARACTERISTICS:
        (A) LENGTH: 857 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 91..798

(xi) SEQUENCE DESCRIPTION: SEQ ID NO:33:

GAAAGGGCTG TCACCCGGCT TGGCCCCTTC CACACCCAAC TGGGGCAAGC CTGACCCGGC      60

GACAGGAGGC ATGAGGGGCC CCCGGCCGAA ATG ACA GTG CTG GCG CCA GCC TGG    114
                                  Met Thr Val Leu Ala Pro Ala Trp
                                   1               5

AGC CCA ACA ACC TAT CTC CTC CTG CTG CTG CTG AGC TCG GGA CTC          162
Ser Pro Thr Thr Tyr Leu Leu Leu Leu Leu Leu Ser Ser Gly Leu
         10                  15                  20

AGT GGG ACC CAG GAC TGC TCC TTC CAA CAC AGC CCC ATC TCC TCC GAC      210
Ser Gly Thr Gln Asp Cys Ser Phe Gln His Ser Pro Ile Ser Ser Asp
 25                  30                  35                  40

TTC GCT GTC AAA ATC CGT GAG CTG TCT GAC TAC CTG CTT CAA GAT TAC      258
Phe Ala Val Lys Ile Arg Glu Leu Ser Asp Tyr Leu Leu Gln Asp Tyr
                 45                  50                  55

CCA GTC ACC GTG GCC TCC AAC CTG CAG GAC GAG GAG CTC TGC GGG GCG      306
Pro Val Thr Val Ala Ser Asn Leu Gln Asp Glu Glu Leu Cys Gly Ala
             60                  65                  70

CTC TGG CGG CTG GTC CTG GCA CAG CGC TGG ATG GAG CGG CTC AAG ACT      354
Leu Trp Arg Leu Val Leu Ala Gln Arg Trp Met Glu Arg Leu Lys Thr
         75                  80                  85

GTC GCT GGG TCC AAG ATG CAA GGC TTG CTG GAG CGC GTG AAC ACG GAG      402
Val Ala Gly Ser Lys Met Gln Gly Leu Leu Glu Arg Val Asn Thr Glu
 90                  95                 100

ATA CAC TTT GTC ACC AAA TGT GCC TTT CAG CCC CCC CCC AGC TGT CTT      450
Ile His Phe Val Thr Lys Cys Ala Phe Gln Pro Pro Pro Ser Cys Leu
105                 110                 115                 120

CGC TTC GTC CAG ACC AAC ATC TCC CGC CTC CTG CAG GAG ACC TCC GAG      498
Arg Phe Val Gln Thr Asn Ile Ser Arg Leu Leu Gln Glu Thr Ser Glu
                125                 130                 135

CAG CTG GTG GCG CTG AAG CCC TGG ATC ACT CGC CAG AAC TTC TCC CGG      546
Gln Leu Val Ala Leu Lys Pro Trp Ile Thr Arg Gln Asn Phe Ser Arg
            140                 145                 150

TGC CTG GAG CTG CAG TGT CAG CCC GAC TCC TCA ACC CTG CCA CCC CCA      594
Cys Leu Glu Leu Gln Cys Gln Pro Asp Ser Ser Thr Leu Pro Pro Pro
        155                 160                 165
```

```
TGG AGT CCC CGG CCC CTG GAG GCC ACA GCC CCG ACA GCC CCG CAG CCC    642
Trp Ser Pro Arg Pro Leu Glu Ala Thr Ala Pro Thr Ala Pro Gln Pro
    170                 175                 180

CCT CTG CTC CTC CTA CTG CTG CTG CCC GTG GGC CTC CTG CTG CTG GCC    690
Pro Leu Leu Leu Leu Leu Leu Leu Pro Val Gly Leu Leu Leu Leu Ala
185                 190                 195                 200

GCT GCC TGG TGC CTG CAC TGG CAG AGG ACG CGG CGG AGG ACA CCC CGC    738
Ala Ala Trp Cys Leu His Trp Gln Arg Thr Arg Arg Arg Thr Pro Arg
                205                 210                 215

CCT GGG GAG CAG GTG CCC CCC GTC CCC AGT CCC CAG GAC CTG CTG CTT    786
Pro Gly Glu Gln Val Pro Pro Val Pro Ser Pro Gln Asp Leu Leu Leu
        220                 225                 230

GTG GAG CAC TGACCTGGCC AAGGCCTCAT CCTGGGGAGG ATACGTAGGC             835
Val Glu His
        235

ACACAGAGGG GAGTCACCAG CC                                            857

(2) INFORMATION FOR SEQ ID NO:34:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO:34:

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60

Gln Asp Glu Glu Leu Cys Gly Ala Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
            180                 185                 190

Pro Val Gly Leu Leu Leu Leu Ala Ala Ala Trp Cys Leu His Trp Gln
        195                 200                 205

Arg Thr Arg Arg Arg Thr Pro Arg Pro Gly Glu Gln Val Pro Pro Val
    210                 215                 220

Pro Ser Pro Gln Asp Leu Leu Leu Val Glu His
225                 230                 235
```

(2) INFORMATION FOR SEQ ID NO:35:

(i) SEQUENCE CHARACTERISTICS:
        (A) LENGTH: 301 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..258

(xi) SEQUENCE DESCRIPTION: SEQ ID NO:35:

```
GGT GCC CCC CGT CCC CAG TCC CCA GGA CCT GCT GCT TGT GGA GCA CTG        48
Gly Ala Pro Arg Pro Gln Ser Pro Gly Pro Ala Ala Cys Gly Ala Leu
 1               5                  10                  15

ACC TGG CCA AGG CCT CAT CCT GGG GAG GAT ACT GAG GCA CAC AGA GGG        96
Thr Trp Pro Arg Pro His Pro Gly Glu Asp Thr Glu Ala His Arg Gly
                20                  25                  30

GAG TCA CCA GCC AGA GGA TGC ATA GCC TGG ACA CAG AGG AAG TTG GCT       144
Glu Ser Pro Ala Arg Gly Cys Ile Ala Trp Thr Gln Arg Lys Leu Ala
             35                  40                  45

AGA GGC CGG TCC CTT CCT TGG GCC CCT CTC ATT CCC TCC CCA GAA TGG       192
Arg Gly Arg Ser Leu Pro Trp Ala Pro Leu Ile Pro Ser Pro Glu Trp
 50                  55                  60

AGG CAA CGC CAG AAT CCA GCA CCG GCC CCA TTT ACC CAA CTC TGT ACA       240
Arg Gln Arg Gln Asn Pro Ala Pro Ala Pro Phe Thr Gln Leu Cys Thr
 65                  70                  75                  80

AAG CCC TTG TCC CCA TGAAATTGTA TATAAATCAT CCTTTTCTAC CAAAAAAAA        295
Lys Pro Leu Ser Pro
                85

AAAAAA                                                                 301
```

(2) INFORMATION FOR SEQ ID NO:36:

(i) SEQUENCE CHARACTERISTICS:
        (A) LENGTH: 85 amino acids
        (B) TYPE: amino acid
        (D) TOPOLOGY: linear (ii) MOLECULE TYPE: protein (xi) SEQUENCE DESCRIPTION: SEQ ID NO:36:

```
Gly Ala Pro Arg Pro Gln Ser Pro Gly Pro Ala Ala Cys Gly Ala Leu
 1               5                  10                  15

Thr Trp Pro Arg Pro His Pro Gly Glu Asp Thr Glu Ala His Arg Gly
                20                  25                  30

Glu Ser Pro Ala Arg Gly Cys Ile Ala Trp Thr Gln Arg Lys Leu Ala
             35                  40                  45

Arg Gly Arg Ser Leu Pro Trp Ala Pro Leu Ile Pro Ser Pro Glu Trp
 50                  55                  60

Arg Gln Arg Gln Asn Pro Ala Pro Ala Pro Phe Thr Gln Leu Cys Thr
 65                  70                  75                  80

Lys Pro Leu Ser Pro
                85
```

(2) INFORMATION FOR SEQ ID NO:37:

(i) SEQUENCE CHARACTERISTICS:
        (A) LENGTH: 1017 base pairs
        (B) TYPE: nucleic acid

```
        (C) STRANDEDNESS: single
        (D) TOPOLOGY: linear (ii) MOLECULE TYPE: cDNA (ix) FEATURE:
        (A) NAME/KEY: CDS
        (B) LOCATION: 100..798

(xi) SEQUENCE DESCRIPTION: SEQ ID NO:37:

GAATTCGCGG CCGCGTCGAG CCTGGCGGGA CTGAGCCCGA GACCTGCCCT CCTGTCACTT      60

CCAAGAACCT GTCACAGGCA TGAGGGGTCC CCGGCAGAG ATG ACA GTG CTG GCG        114
                                            Met Thr Val Leu Ala
                                              1               5

CCA GCC TGG AGC CCA AAT TCC TCC CTG TTG CTG CTG TTG CTG CTG CTG      162
Pro Ala Trp Ser Pro Asn Ser Ser Leu Leu Leu Leu Leu Leu Leu Leu
                10                  15                  20

AGT CCT TGC CTG CGG GGG ACA CCT GAC TGT TAC TTC AGC CAC AGT CCC      210
Ser Pro Cys Leu Arg Gly Thr Pro Asp Cys Tyr Phe Ser His Ser Pro
            25                  30                  35

ATC TCC TCC AAC TTC AAA GTG AAG TTT AGA GAG TTG ACT GAC CAC CTG      258
Ile Ser Ser Asn Phe Lys Val Lys Phe Arg Glu Leu Thr Asp His Leu
        40                  45                  50

CTT AAA GAT TAC CCA GTC ACT GTG GCC GTC AAT CTT CAG GAC GAG AAG      306
Leu Lys Asp Tyr Pro Val Thr Val Ala Val Asn Leu Gln Asp Glu Lys
    55                  60                  65

CAC TGC AAG GCC TTG TGG AGC CTC TTC CTA GCC CAG CGC TGG ATA GAG      354
His Cys Lys Ala Leu Trp Ser Leu Phe Leu Ala Gln Arg Trp Ile Glu
 70                 75                  80                  85

CAA CTG AAG ACT GTG GCA GGG TCT AAG ATG CAA ACG CTT CTG GAG GAC      402
Gln Leu Lys Thr Val Ala Gly Ser Lys Met Gln Thr Leu Leu Glu Asp
                90                  95                 100

GTC AAC ACC GAG ATA CAT TTT GTC ACC TCA TGT ACC TTC CAG CCC CTA      450
Val Asn Thr Glu Ile His Phe Val Thr Ser Cys Thr Phe Gln Pro Leu
            105                 110                 115

CCA GAA TGT CTG CGA TTC GTC CAG ACC AAC ATC TCC CAC CTC CTG AAG      498
Pro Glu Cys Leu Arg Phe Val Gln Thr Asn Ile Ser His Leu Leu Lys
        120                 125                 130

GAC ACC TGC ACA CAG CTG CTT GCT CTG AAG CCC TGT ATC GGG AAG GCC      546
Asp Thr Cys Thr Gln Leu Leu Ala Leu Lys Pro Cys Ile Gly Lys Ala
    135                 140                 145

TGC CAG AAT TTC TCT CGG TGC CTG GAG GTG CAG TGC CAG CCG GAC TCC      594
Cys Gln Asn Phe Ser Arg Cys Leu Glu Val Gln Cys Gln Pro Asp Ser
150                 155                 160                 165

TCC ACC CTG CTG CCC CCA AGG AGT CCC ATA GCC CTA GAA GCC ACG GAG      642
Ser Thr Leu Leu Pro Pro Arg Ser Pro Ile Ala Leu Glu Ala Thr Glu
                170                 175                 180

CTC CCA GAG CCT CGG CCC AGG CAG CTG TTG CTC CTG CTG CTG CTG CTG      690
Leu Pro Glu Pro Arg Pro Arg Gln Leu Leu Leu Leu Leu Leu Leu Leu
            185                 190                 195

CTG CCT CTC ACA CTG GTG CTG CTG GCA GCC GCC TGG GGC CTT CGC TGG      738
Leu Pro Leu Thr Leu Val Leu Leu Ala Ala Ala Trp Gly Leu Arg Trp
        200                 205                 210

CAA AGG GCA AGA AGG AGG GGG GAG CTC CAC CCT GGG GTG CCC CTC CCC      786
Gln Arg Ala Arg Arg Arg Gly Glu Leu His Pro Gly Val Pro Leu Pro
    215                 220                 225

TCC CAT CCC TAGGATGCGA GCCTTGTGCA TCGTTGACTC AGCCAGGGTC              835
Ser His Pro
230

TTATCTCGAG TTGGGAACCA AAACAAGGAA CAAGCTAGGC AAGTGCTGTG CTGAGTTACA    895
```

```
TCCCCAGCCC AGAGGACACA CTGTCTGGGT ATGGCGATGG ACACTGTAAT TCCAGTGCTT      955

CTGGATTGGA CATGCTGAAA CTGGATACTG ACTTTAAGAA AAACAGAAAG GAAGAACCCC     1015

CC                                                                    1017
```

(2) INFORMATION FOR SEQ ID NO:38:

(i) SEQUENCE CHARACTERISTICS:
        (A) LENGTH: 232 amino acids
        (B) TYPE: amino acid
        (D) TOPOLOGY: linear (ii) MOLECULE TYPE: protein (xi) SEQUENCE DESCRIPTION: SEQ ID NO:38:

```
Met Thr Val Leu Ala Pro Ala Trp Ser Pro Asn Ser Leu Leu Leu
 1               5                  10                  15

Leu Leu Leu Leu Leu Ser Pro Cys Leu Arg Gly Thr Pro Asp Cys Tyr
                20                  25                  30

Phe Ser His Ser Pro Ile Ser Ser Asn Phe Lys Val Lys Phe Arg Glu
            35                  40                  45

Leu Thr Asp His Leu Leu Lys Asp Tyr Pro Val Thr Val Ala Val Asn
 50                  55                  60

Leu Gln Asp Glu Lys His Cys Lys Ala Leu Trp Ser Leu Phe Leu Ala
 65                  70                  75                  80

Gln Arg Trp Ile Glu Gln Leu Lys Thr Val Ala Gly Ser Lys Met Gln
                85                  90                  95

Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
            115                 120                 125

Ser His Leu Leu Lys Asp Thr Cys Thr Gln Leu Leu Ala Leu Lys Pro
130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gln Leu Leu Leu
            180                 185                 190

Leu Leu Leu Leu Leu Leu Pro Leu Thr Leu Val Leu Leu Ala Ala Ala
            195                 200                 205

Trp Gly Leu Arg Trp Gln Arg Ala Arg Arg Arg Gly Glu Leu His Pro
210                 215                 220

Gly Val Pro Leu Pro Ser His Pro
225                 230
```

(2) INFORMATION FOR SEQ ID NO:39:

(i) SEQUENCE CHARACTERISTICS:
        (A) LENGTH: 344 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..174

(xi) SEQUENCE DESCRIPTION: SEQ ID NO:39:

-continued

```
GGTAACGGTG GCCCCAGAGC CCAGCACCAT GGTGCCACCA GGCTCACAGC CACAGCCTTG    60

CTAACTGTGT GTCCAGGGCT TCTGCTCCCA CTAGTTGGCA CTTCACACAT GTTCTTTCTC   120

CCTTATTTTC TCTCTTTTCT TTCTTCTTTT TTAAAGATGT ATCTTTATGT GTGAGTGTTT   180

TACCTACATG CCTGTAAGTG CACTGAATGT GTGTCTGGTG CCTGCAGAGG CCAGAAGAGG   240

GCACCAGATC CCCTGAAACT GGAGTCTCTN NGCTCCGTGT GAACCACCAC GTGGTGCTGG   300

GACCCAGGTC CAATGCAAGA GCACCCAGGG TTCTTACCTG CTGA                    344
```

(2) INFORMATION FOR SEQ ID NO:40:

(i) SEQUENCE CHARACTERISTICS:
        (A) LENGTH: 57 amino acids
        (B) TYPE: amino acid
        (D) TOPOLOGY: linear (ii) MOLECULE TYPE: peptide (xi) SEQUENCE DESCRIPTION: SEQ ID NO:40:

```
Gly Asn Gly Gly Pro Arg Ala Gln His His Gly Ala Thr Arg Leu Thr
1               5                   10                  15

Ala Thr Ala Leu Leu Thr Val Cys Pro Gly Leu Leu Leu Pro Leu Val
            20                  25                  30

Gly Thr Ser His Met Phe Phe Leu Pro Tyr Phe Leu Ser Phe Leu Ser
        35                  40                  45

Ser Phe Leu Lys Met Tyr Leu Tyr Val
    50                  55
```

(2) INFORMATION FOR SEQ ID NO:41:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..87

(xi) SEQUENCE DESCRIPTION: SEQ ID NO:41:

```
GAT AGG GTC TCA TTA TTA TGC AGG CTA GGC CTG ACC CTG AAC TCA AAG     48
Asp Arg Val Ser Leu Leu Cys Arg Leu Gly Leu Thr Leu Asn Ser Lys
1               5                   10                  15

CAA TCC TCC TGC CTC AGT GTC CTG AGT GCT GGG ATT ACA                 87
Gln Ser Ser Cys Leu Ser Val Leu Ser Ala Gly Ile Thr
            20                  25
```

(2) INFORMATION FOR SEQ ID NO:42:

(i) SEQUENCE CHARACTERISTICS:
        (A) LENGTH: 29 amino acids
        (B) TYPE: amino acid
        (D) TOPOLOGY: linear -continued (ii) MOLECULE TYPE: protein (xi) SEQUENCE DESCRIPTION: SEQ ID NO:42:

Asp Arg Val Ser Leu Leu Cys Arg Leu Gly Leu Thr Leu Asn Ser Lys
1               5                   10                  15

Gln Ser Ser Cys Leu Ser Val Leu Ser Ala Gly Ile Thr
            20                  25

ANTIBODIES THAT BIND PURIFIED MAMMALIAN FLT3 LIGANDS

The present invention is a divisional of patent application U.S. Ser. No. 08/261,553, filed Jun. 17, 1994; now abandoned which is a continuation-in-part of commonly assigned patent application U.S. Ser. No. 08/162,413, filed Dec. 3, 1993, since abandoned; which was a continuation-in-part of commonly assigned then patent application U.S. Ser. No. 08/155,111, filed Nov. 19, 1993, since abandoned; which was a continuation-in-part of commonly assigned then patent application U.S. Ser. No. 08/112,391, filed Aug. 24, 1993, since abandoned; which was a continuation-in-part of commonly assigned then patent application U.S. Ser. No. 08/106,340, filed Aug. 13, 1993, since abandoned; which was a continuation-in-part of commonly assigned then patent application U.S. Ser. No. 08/092,549, filed Jul. 16, 1993, since abandoned; which was a continuation-in-part of commonly assigned then U.S. patent application Ser. No. 08/089,263, file Jul. 7, 1993, now abandoned which was a continuation-in-part of then patent application U.S. Ser. No. 08/065,231, filed May 19, 1993, since abandoned.

FIELD OF THE INVENTION

The present invention relates to compositions related to proteins which function in controlling development and differentiation of mammalian cells, e.g., cells of a mammalian immune system. In particular, it provides proteins and mimetics which regulate development, differentiation, and function of various cell types, including hematopoietic cells.

BACKGROUND OF THE INVENTION

Protein tyrosine kinases often play important roles in signal transduction leading to cellular proliferation. The large family of protein tyrosine kinases includes many growth factor receptors. See, e.g., Pawson, et al. (1990) *Trends in Genetics* 6:350-356. Growth factor receptors are important in control and regulation of cellular physiology and development. Although these receptors have been found on various cell lineages, their specific roles in regulation of development of different cell lineages are generally poorly understood. Suggestions of a role for a protein tyrosine kinase in hematopoiesis have been largely based upon the identification of the c-kit receptor tyrosine kinase as the W locus, mutations in which affect erythroid and mast cell lineages. See, e.g., Chabot, et al. (1988) *Nature* 335:88-89; and Geissler, et al. (1988) *Cell* 55:185-192.

Besides the gene product of the W locus, another protein tyrosine kinase had been isolated and characterized. See Matthews, et al. (1991) *Cell* 65:1143-1152; and Rosnet, et al. (1991) *Oncogene* 6:1641-1650. This protein has been designated Fms-like tyrosine kinase 3 (Flt3) or Flk2. Although it has been localized to particular cell types, e.g., placenta, gonad, neural, and hematopoietic, its biological effects on cell differentiation and physiology have not been fully described.

Moreover, the receptor should mediate cellular signal transduction in response to a natural ligand. The nature of the ligand has yet to be identified, and its physiological effects and cell lineage specificity remain undescribed. However, the distribution of the receptor suggests that the ligand has a role in regulating cell physiology and development in a multiplicity of cell lineages.

The absence of knowledge about the structural, biological, and physiological properties of the regulatory factors which naturally bind to the Flt3 tyrosine kinase receptor prevents the modulation of the effects of the factors. Medical conditions where regulation of the development or physiology of relevant cells thus remain unmanageable. However, the present invention provides solutions to these and many other problems.

SUMMARY OF THE INVENTION

The present invention is based, in part, upon the discovery of natural ligands for the Flt3 tyrosine kinase receptor. It embraces agonists and antagonists of the natural ligands, e.g., mutations (muteins) of the natural sequences, fusion proteins, chemical mimetics, antibodies, and other structural or functional analogues. It is also directed to isolated genes encoding proteins of the invention. Various uses of these different protein or nucleic acid compositions are also provided.

The present invention provides substantially pure Flt3 ligands or peptides thereof, or fusion proteins comprising Flt3 ligand sequence; antibodies specific for binding to a Flt3 ligand; and a nucleic acid encoding a Flt3 ligand or fragment thereof.

In substantially pure Flt3 ligand or peptide thereof embodiments, the ligand or peptide can be from a warm blooded animal selected from the group of birds and mammals, including a mouse; comprise at least one polypeptide segment of Table 1; exhibit a post-translational modification pattern distinct from natural Flt3 ligand; exhibit at least one of the features disclosed in Table 2; or induce Flt3 receptor to self phosphorylate. A further embodiment is a composition comprising such a ligand and a pharmaceutically acceptable carrier.

In antibody embodiments, the antigen can be a mammalian protein, including a mouse; the antibody is raised against a peptide sequence of Table 1; the antibody is a monoclonal antibody; or the antibody is labeled.

In nucleic acid embodiments, the nucleic acid can comprise a sequence of Table 3.

The invention also embraces a kit comprising a substantially pure Flt3 ligand or fragment, e.g., as a positive control; an antibody or receptor which specifically binds a Flt3 ligand; or a nucleic acid encoding a Flt3 ligand or peptide.

The availability of these reagents also provides methods of modulating physiology or development of a cell comprising contacting said cell with an agonist or antagonist of a Flt3 ligand. For example, the antagonist might be an antibody against a mammalian Flt3 ligand or the cell may be a hematopoietic cell, including a lymphoid cell; a placenta cell; a gonad cell; or a neural cell, including neuronal or non-neuronal cells. The treatment may be directed to circumstances where repopulation of the hematopoietic compartment needs to be accelerated, e.g., following radiation or chemotherapy and/or bone marrow transplantation, where neutropenia or thrombocytopenia is exhibited. Alternatively, the compositions will be useful where certain hematopoietic compartments have proliferated abnormally.

DETAILED DESCRIPTION OF THE PREFERRED EMBODIMENTS

Figure 1:
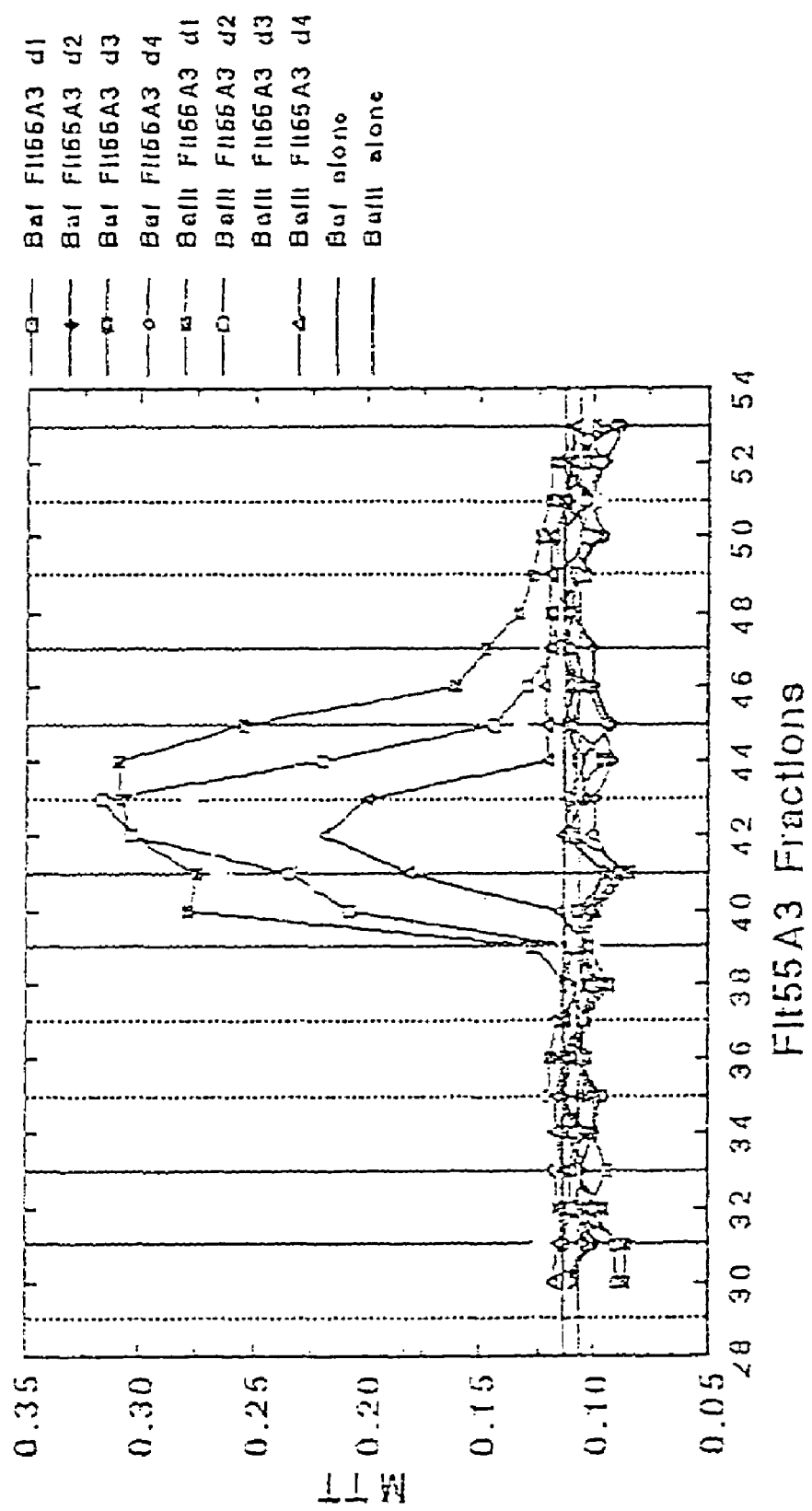
FIG. 1 shows the activity profile of a preparation of purified Flt3 ligand from reverse phase chromatography.

Outline
I. General
II. Purified Flt3 Ligand
  A. physical properties
  B. biological properties
III. Physical Variants
  A. sequence variants, fragments
  B. post-translational variants
    1. glycosylation
    2. others
IV. Functional Variants
  A. analogues; fragments
    1. agonists
    2. antagonists
  B. mimetics
    1. protein
    2. chemicals
  C. species variants
V. Antibodies
  A. polyclonal
  B. monoclonal
  C. fragments, binding compositions
VI. Nucleic Acids
  A. natural isolates; methods
  B. synthetic genes
  C. methods to isolate
VII. Making Flt3 Ligand; Mimetics
  A. recombinant methods
  B. synthetic methods
  C. natural purification
VIII. Uses
  A. diagnostic
  B. therapeutic
IX. Kits
  A. nucleic acid reagents
  B. protein reagents
  C. antibody reagents I. General The present invention provides the amino acid sequence and DNA sequences encoding various mammalian proteins which exhibit properties of binding to a tyrosine kinase receptor protein. These proteins are designated Flt3 ligands because they were initially characterized as proteins which bind to the Flt3 protein, a protein which exhibits structural characteristics of a tyrosine kinase type of receptor. The natural ligands are capable of mediating various biochemical responses which should lead to biological or physiological responses in target cells. Initial studies had localized the protein to hematopoietic stem cells and primitive uncommitted progenitors. The best characterized embodiment was initially described in mouse, but human variants are also described herein. Additional sequences for proteins in other mammalian species, e.g., human, should also be available. The descriptions below are directed, for exemplary purposes, to a mouse Flt3 ligand, but are likewise applicable to related embodiments from other species.

Isolated mouse Flt3 protein was recently described as a protein which exhibits structural features of a receptor tyrosine kinase. The protein is localized in placenta, gonad, hematopoietic, and neural tissues, among others. See Matthews, et al. (1991) *Cell* 65:1143-1152; and Rosnet, et al. (1991) *Oncogene* 6:1641-1650. The Flt3 receptor mediates a biochemical response to binding of a heretofore unidentified ligand leading to signal transduction and cellular response. In particular, the ligand has been isolated by pursuing a self-phosphorylation assay, which likely reflects cross phosphorylation of dimerized receptor molecules. The ligand has been isolated and characterized as a protein which migrates on polyacrylamide gel electrophoresis with a mobility characteristic of a protein of about 30 kD, while other physical properties are described in Table 2.

The ligand for Flt3 should be present in the mentioned tissue types and the interaction of the ligand with receptor should be important for mediating various aspects of cellular physiology or development. The distribution of the Flt3 receptor protein in different tissues suggests that it and its ligand have functional roles outside the immune system, e.g., in developmental regulation in other cell types. See, e.g., Gilbert (1991) *Developmental Biology* (3d ed.), Sinauer Associates, Sunderland, Mass.; Browder, et al. (1991) *Developmental Biology* (3d ed.), Saunders, Philadelphia, Pa.; Russo, et al. (1992) *Development: The Molecular Genetic Approach*, Springer-Verlag, New York, N.Y.; and Wilkins (1993) *Genetic Analysis of Animal Development* (2d ed.) Wiley-Liss, New York, N.Y.

When highly purified native mouse Flt3 ligand was added with IL-3 to mouse $Thy^{lo}$ $Sca-1^+$ $lin^-$ stem cells, colony numbers were significantly increased. These conditions produced multilineage colonies, but they did not contain the abundant erythroid cells characteristically found with c-kit ligand and IL-3. A modest co-stimulatory activity was evident in the presence of Flt3 ligand and IL-6. However, Flt3 ligand alone had no stimulatory activity on these cells even when used in combination with c-kit ligand. When sorted human fetal liver progenitor cells were used, Flt3 ligand had a similar synergistic effect in combination with GM-CSF or IL-3. In this case, the co-stimulatory effects of Flt3 ligand were observed on both low proliferative potential colony-forming cells (LPP-CFC) as well as the more primitive high proliferative potential colony-forming cells (HPP-CFC). However, in contrast to c-kit ligand, Flt3 ligand was not able to augment the growth of human fetal liver burst-forming units erythroid (BFU-E). Thus, Flt3 ligand enhances the response of stem and primitive progenitor cells to growth factors but in a manner distinct from c-kit ligand.

With respect to myeloid progenitors, Flt3 ligand has little effect alone on proliferation, but in combination with such factors as GM-CSF or IL-3, the ligand synergistically can promote the growth of both primitive and more mature myeloid precursors. Other observations show that the Flt3 ligand, in combination with other specific cytokines, can stimulate proliferation of human B cell progenitors.

Flt3 ligand, in combination with IL-7 or IL-12, activates specific thymocyte subsets to proliferate. $CD4^+$, $CD8^+$, and $CD4^{lo}$ thymocytes are some of the subsets responding to the cytokine combinations.

Flt3 ligand was also tested on day 14 fetal thymocytes which are enriched for T cell precursors. Flt3 ligand alone had little effect but in combination with IL-12 induced significant proliferation. IL-12 also induces proliferation of fetal thymocytes in combination with c-kit ligand. These results support a further role for Flt3 ligand in T cell development.

Identification of the ligand for Flt3 provides means to address some of the questions raised by these observations. More particularly, the Flt3 ligand has differences from kit ligand in its effect on stem cell populations. The Flt3 ligand, therefore, will likely have different side effects from preexisting therapies. Perhaps most importantly, the Flt3 ligand will be useful in treating various effects of radiation or chemo-therapies and/or bone marrow transplantation. Such treatments typically lead to depletion of many hematopoietic cell populations, both lymphoid (including B, T, and NK cells) and myeloid (including erythroid cells, macrophages, neutrophils, megakaryocytes, and mast cells). The most significant effect is usually a depletion of neutrophils (neutropenia) and/or platelets (thrombocytopenia). The activities described indicate that Flt3 ligand will be useful in treatment of myeloid and/or lymphoid cell deficiencies. Alternatively, antagonists may be useful in modulating of conditions of excessive proliferation of these cell types, e.g., particular neoplastic conditions, including chronic myeloid leukemias. See, e.g., Berkow (ed.) *The Merck Manual of Diagnosis and Therapy*, Merck & Co., Rahway, N.J.; and Thorn, et al. *Harrison's Principles of Internal Medicine*, McGraw-Hill, N.Y.

II. Purified Flt3 Ligand

Mouse and human Flt3 ligand amino acid sequences are shown in Table 1. These sequences correspond to SEQ ID NO: 1 through 23. These amino acid sequences, provided amino to carboxy, are important in providing sequence information in the ligand allowing for distinguishing the protein from other proteins. Moreover, the peptide sequences allow preparation of peptides to generate antibodies to recognize such segments, and allow preparation of oligonucleotide probes, both of which are strategies for isolation, e.g., cloning, of genes encoding such sequences. In particular, the MB8 isolate contains an insert of 29 amino acids which contain proteolytic processing sites which will allow the helical cytokine domain of the ligand to be cleaved from a membrane attachment. Similarities have been observed with other cytokines. See, e.g., Bosenberg, et al. (1992) *Cell* 71:1157-1165; Huang, et. al. (1992) *Molecular Biology of the Cell* 3:349-362; and Pandiella, et al. (1992) *J. Biol. Chem.* 267: 24028-24033. This will avoid certain problems of working with, or administering, a cell bound protein, and provides insight into possible mechanisms of cellular specificity.

TABLE 1

Flt3 ligand peptide fragment sequences.

```
 1. FVQT(N/C/S/T)I(S) (H)LLK
 2. DYPVTVAV(N)LQ(D)E(K)
 3. TPD(V/A)YF(S) (H) (S)PIS(S) (N) (F) (K)
 4. WIEQLK(Q) (P) (G) (S)
 5. ELT(V) (H)LLK
 6. ILFXLFLQ(Y) (R)
 7. S(H) (S)PISSNF
 8. (W) IEQLK
 9. DYPVTVAVNLQ
10. DAYFSHSPISSNFKVKFREL(T) (V)
11. DYPVTVA(A)

thus providing consensus sequences:

12. TPDAYFSHSPISSNFKVKFRELTVHLLK
13. WIEQLK
14. FVQTXISHLLK
15. ILFXLFAQYR
16. DYPVTVAVNLQ however, alignment with other ligands for Flt3-like
receptors and other considerations suggests an amino terminal
sequence of the mature protein:

17. TPDCYFSHSP ISSNFKVKFR ELT(V)HLLKDY PVTVAVNLQD EK and nucleic acid sequencing of a clone provides the
following sequence:

18. TPDCYFSHSP ISSNFKVKFR ELTDHLLKDY PVTVAVNLQD EKHCKALWSL
    FLAQRWIEQL KTVAGSKMQT LLEDVNTEIH FVTSCTFQPL PECLRFVQTN
    I five different mammalian variants have the following
sequences: (for T118 see SEQ ID NO: 40; for T110 see SEQ ID NO: 38;
for S109 see SEQ ID NO: 36; for S86 see SEQ ID NO: 34; and for MB8
see SEQ ID NO: 42)

MoT118/T110   M T V V E P A W S P N S S L L L L L L L L S P C L   25
HuS86/S109    M T V L A P A W S P . T T Y L L L L L L L S S G L   24

MoT118/T110   R G T P D C Y F S H S P I S S N F K V K F R E L T   50
HuS86/S109    S G T Q D C S F Q H S P I S S D F A V K I R E L S   49

MoT118/T110   D H L L K D Y P V T V A V N L Q D E K H C K A L W   75
HuS86/S109    D Y L L Q D Y P V T V A S N L Q D E E L C G A L W   74

MoT118/T110   S L F L A Q R W I E Q L K T V A G S K M Q T L L E   100
HuS86/S109    R L V L A Q R W M E R L K T V A G S K M Q G L L E   99

Mot118B/T110  D V N T E I H F V T S C T F N P L P E C L R F V Q   125
HuS86/S109    R V N T E I H F V T K C A F Q P P P S C L R F V Q   124

MoT118/T110   T N I S H L L K D T C T Q L L A L K P C I G K A C   150
```

TABLE 1-continued

Flt3 ligand peptide fragment sequences.

| HuS86/S109 | T N I S R L L Q E T S E Q L V A L K P W I T R . . | 147 |
|---|---|---|
| | • | |
| MoT118 | Q N F S R C L E V Q C Q P G N G G P R A Q H H G A | 175 |
| MoT110 | Q N F S R C L E V Q C Q P D S S T L L P P R S P I | 175 |
| HuS86 | Q N F S R C L E L Q C Q P D S S T L P P P W S P R | 172 |
| HuS109 | Q N F S R C L E L Q C Q P G A P R P Q S P G P A A | 172 |
| MoT1188 | T R L T A T A L L T V C P G L L L P L V G T S H M | 200 |
| MoT110 | A L E A T E L P E P R P R Q L L L L L L L L P L | 200 |
| HuS86 | P L E A T A P T A P Q P P L L L L L L P V G L L L | 197 |
| HuS109 | C G A L T W P R P H P G E D T E A H R G E S P A R | 197 |
| MoT118 | F F L P Y F L S F L S S F L K M Y L Y V | 220 |
| MoT100 | T L V L L A A W G L R W Q R A R R R G E L H P G . | 224 |
| HuS86 | . . . L A A A W C L H W Q R T R R R T P R P G E Q | 219 |
| Hu109 | G C I A W T Q R K L A R G R S L P W A P L I P S P | 222 |
| MoT110 | V . P L P S H P | 231 |
| HuS86 | V P P V P S P Q D L L L V E H | 234 |
| Hu109 | E W R Q R Q N P A P A P F T Q L C T K P L S P | 245 | bold residues are conserved wfth CSF's; underlined sequences are
peptide sequences described above;
# is the position of an insert in one clone;
• indicates where divergence of sequences in variant isolates begins
and the insertion point of the 29 amino acid insert found in the MB8
isolate.
The MB8 isolate has a 29 amino acid insert with the sequence: DRVS-
LLCRLGLTLNSLQSSCL-SVLSAGIT.

TABLE 2

Physical properties of mouse Flt3 ligand.

SDS-Polyacrylamide gel electrophoresis: reduced migration
approximately 30 Kd; seemingly a glycoprotein.
Ammonium Sulfate precipitation (at 4° C.): activity found in 60-
85% saturated $(NH_4)_2SO_4$ pellet.
Hydrophobic Interaction Chromatography [$(NH_4)_2SO_4$ gradient in 20
mM Tris, pH 7.5 on a Phenyl-5 PW column]: activity eluted between
900-750 mM $(NH_4)_2SO_4$.
Anion Exchange Chromatography (NaCl gradient in 20 mM Tris, pH
7.5 on Mono Q column): activity eluted between 130-250 mM NaCl.
Cation Exchange Chromatography (NaCl gradient in 10 mM citrate,
pH 3.0 on Mono S column): the bulk of the activity eluted
between 440-540 mM NaCl.
Gel Filtration (Sephacryl S200 column): the activity ran with an
apparent molecular weight of 70 kD.
Reversed Phase HPLC (water to acetonitrile gradient in 0.1% TFA
on a Poros R/H column): the activity eluted between 32-35%
acetonitrile.

As used herein, the term "mouse Flt3 ligand" shall encompass, when used in a protein context, a protein having mouse amino acid sequences shown in Table 1, or a significant fragment of such a protein. It also refers to a mouse derived polypeptide which exhibits similar biological function or interacts with Flt3 ligand specific binding components. These binding components, e.g., antibodies, typically bind to a Flt3 ligand with high affinity, e.g., at least about 100 nM, usually better than about 30 nM, preferably better than about 10 nM, and more preferably at better than about 3 nM. Homologous proteins would be found in mammalian species other than mouse, e.g., rats. Non-mammalian species should also possess structurally or functionally related genes and proteins.

The term "polypeptide" as used herein includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22' amino acids, more usually at least 24 amino acids, preferably at least 26 amino acids, more preferably at least 28 amino acids, and, in particularly preferred embodiments, at least about 30 or more amino acids.

The term "binding composition", refers to molecules that bind with specificity to Flt3 ligand, e.g., in a ligand-receptor type fashion or an antibody-antigen interaction. These compositions may be compounds, e.g., proteins, which specifically associate with Flt3 ligand, including natural physiologically relevant protein-protein interactions, either covalent or non-covalent. The binding composition may be a polymer, or another chemical reagent. No implication as to whether the Flt3 ligand presents a concave or convex shape in its ligand-receptor interaction is represented, other than the interaction exhibit similar specificity, e.g., specific affinity. A functional analog may be a ligand with structural modifications, or may be a wholly unrelated molecule, e.g., which has a molecular shape which interacts with the appropriate ligand binding determinants. The ligands may serve as agonists or antagonists of the receptor, see, e.g., Goodman, et al. (eds.) (1990) *Goodman & Gilman's: The Pharmacological Bases of Therapeutics* (8th ed.), Pergamon Press.

Substantially pure typically means that the protein is free from other contaminating proteins, nucleic acids, and other biologicals derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in most preferred embodiments, at least 99% pure.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the ligand.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W.H. Freeman; and Cantor and Schimmel (1980) *Biophysical Chemistry*, parts 1-3, W.H. Freeman & Co., San Francisco. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30 S, more typically less than about 15 S, usually less than about 10 S, more usually less than about 6 S, and, in particular embodiments, preferably less than about 4 S, and more preferably less than about 3 S.

Two specific biological activities of the Flt3 ligand are described below. The first is a ligand-dependent activity conferred on receptor-transformed or appropriate test cells. The second is a ligand-dependent autophosphorylation of receptor. These two biological activities have been utilized to isolate an appropriate ligand. Other biological activities are also described.

III. Physical Variants

This invention also encompasses proteins or peptides having substantial amino acid sequence homology with the amino acid sequence of the Flt3 ligand. The variants include species or allelic variants.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25-100% homology (if gaps can be introduced), to 50-100% homology (if conservative substitutions are included) with the amino acid sequence of the Flt3 ligand. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443-453; Sankoff, et al. (1983) *Chapter One in Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.

The isolated Flt3 ligand DNA can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Such mutant Flt3 ligand derivatives include predetermined or site-specific mutations of the respective protein or its fragments. "Mutant Flt3 ligand" encompasses a polypeptide otherwise falling within the homology definition of the mouse Flt3 ligand as set forth above, but having an amino acid sequence which differs from that of Flt3 ligand as found in nature, whether by way of deletion, substitution, or insertion. In particular, "site specific mutant Flt3 ligand" generally includes proteins having significant homology with a ligand having sequences of Table 1, and as sharing various biological activities, e.g., antigenic or immunogenic, with those sequences, and in preferred embodiments contain most of the disclosed sequences. Similar concepts apply to different Flt3 ligand proteins, particularly those found in various warm blooded animals, e.g., mammals and birds. As stated before, it is emphasized that descriptions are generally meant to encompass all Flt3 ligand proteins, not limited to the mouse embodiment specifically discussed.

Although site specific mutation sites are predetermined, mutants need not be site specific. Flt3 ligand mutagenesis can be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a Flt3 ligand polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, ligand-binding or other segments may be "swapped" between different new fusion polypeptides or fragments. See, e.g., Cunningham, et al. (1989) *Science* 243:1330-1336; and O'Dowd, et al. (1988) *J. Biol. Chem.* 263:15985-15992. Thus, new chimeric polypeptides exhibiting new combinations of specificities will result from the functional linkage of ligand-binding specificities and other functional domains.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

IV. Functional Variants

The blocking of physiological response to Flt3 ligands may result from the inhibition of binding of the ligand to the Flt3 receptor, likely through competitive inhibition. Thus, in vitro assays of the present invention will often use isolated protein, membranes from cells expressing a recombinant membrane associated Flt3 ligand, soluble fragments comprising receptor binding segments of these ligands, or fragments attached to solid phase substrates. These assays will also allow for the diagnostic determination of the effects of either binding segment mutations and modifications, or ligand mutations and modifications, e.g., ligand analogues.

This invention also contemplates the use of competitive drug screening assays, e.g., where neutralizing antibodies to antigen or receptor fragments compete with a test compound for binding to the protein. In this manner, the antibodies can be used to detect the presence of any polypeptide which shares one or more antigenic binding sites of the ligand and can also be used to occupy binding sites on the protein that might otherwise interact with a receptor.

Additionally, neutralizing antibodies against Flt3 ligand and soluble fragments of the ligand which contain a high affinity receptor binding site, can be used to inhibit ligand function in tissues, e.g., tissues experiencing abnormal physiology.

"Derivatives" of Flt3 ligand antigens include amino acid sequence mutants, glycosylation variants, and covalent or aggregate conjugates with other chemical moieties. Covalent derivatives can be prepared by linkage of functionalities to groups which are found in Flt3 ligand amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the Flt3 ligand or fragments thereof with other proteins or polypeptides. These derivatives can be synthesized in recombinant culture such as N- or C-terminal fusions or by the use of agents known in the art for their usefulness in cross-linking proteins through reactive side groups. Preferred ligand derivatization sites with cross-linking agents are at free amino groups, carbohydrate moieties, and cysteine residues.

Fusion polypeptides between Flt3 ligands and other homologous or heterologous proteins are also provided. Many growth factors and cytokines are homodimeric entities, and a repeat construct may have various advantages, including lessened susceptibility to proteolytic cleavage. Moreover, many receptors require dimerization to transduce a signal, and various dimeric ligands or domain repeats can be desirable. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a ligand, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812-816.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant-nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1-3, Cold Spring Harbor Laboratory. Techniques for synthesis of polypeptides are described, for example, in Merrifield (1963) *J. Amer. Chem. Soc.* 85:2149-2156; Merrifield (1986) *Science* 232: 341-347; and Atherton, et al. (1989) *Solid Phase Peptide Synthesis: A Practical Approach*, IRL Press, oxford.

This invention also contemplates the use of derivatives of Flt3 ligands other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a Flt3 ligand antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-Flt3 ligand antibodies or its receptor. The Flt3 ligands can also be labeled with a detectable group, for example radioiodinated by the chloramine T procedure, covalently bound to rare earth chelates, or conjugated to another fluorescent moiety for use in diagnostic assays. Purification of Flt3 ligand may be effected by immobilized antibodies or receptor.

A solubilized Flt3 ligand or fragment of this invention can be used as an immunogen for the production of antisera or antibodies specific for the ligand or any fragments thereof. The purified ligands can be used to screen monoclonal antibodies or ligand-binding fragments prepared by immunization with various forms of impure preparations containing the protein. In particular, the term "antibodies" also encompasses antigen binding fragments of natural antibodies. Purified Flt3 ligands can also be used as a reagent to detect antibodies generated in response to the presence of elevated levels of the ligand or cell fragments containing the ligand, both of which may be diagnostic of an abnormal or specific physiological or disease condition. Additionally, ligand fragments may also serve as immunogens to produce the antibodies of the present invention, as described immediately below. For example, this invention contemplates antibodies raised against amino acid sequences encoded by nucleotide sequences shown in Table 1, or fragments of proteins containing them. In particular, this invention contemplates antibodies having binding affinity to or being raised against specific fragments which are predicted to lie outside of the lipid bilayer.

The present invention contemplates the isolation of additional closely related species variants. Southern and Northern blot analysis should establish that similar genetic entities exist in other mammals. It is likely that Flt3 ligands are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the ligands will be greatly accelerated by the isolation and characterization of distinct species variants of the ligands. In particular, the present invention provides useful probes for identifying additional homologous genetic entities in different species.

The isolated genes will allow transformation of cells lacking expression of a corresponding Flt3 ligand, e.g., either species types or cells which lack corresponding ligands and exhibit negative background activity. Expression of transformed genes will allow isolation of antigenically pure cell lines, with defined or single specie variants. This approach will allow for more sensitive detection and discrimination of the physiological effects of any Flt3 receptor proteins. Subcellular fragments, e.g., cytoplasts or membrane fragments, can be isolated and used.

Dissection of critical structural elements which effect the various differentiation functions provided by ligands is possible using standard techniques of modern molecular biology, particularly in comparing members of the related class. See, e.g., the homolog-scanning mutagenesis technique described in Cunningham, et al. (1989) *Science* 243:1339-1336; and approaches used in O'Dowd, et al. (1988) *J. Biol. Chem.* 263:15985-15992; and Lechleiter, et al. (1990) *EMBO J.* 9:4381-4390.

In particular, receptor binding segments can be substituted between species variants to determine what structural features are important in both receptor binding affinity and specificity, as well as signal transduction. An array of different ligand variants will be used to screen for ligands exhibiting combined properties of interaction with different receptor species variants.

Intracellular functions would probably involve segments of the receptor which are normally accessible to the cytosol. However, ligand internalization may occur under certain circumstances, and interaction between intracellular components and "extracellular" segments may occur. The specific segments of interaction of Flt3 ligand with other intracellular components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of Flt3 ligand will be pursued. The controlling elements associated with the ligands may exhibit differential developmental, tissue specific, or other expression patterns. Upstream or downstream genetic regions, e.g., control elements, are of interest. In particular, developmental or physiological variants, e.g., multiple alternatively processed forms of ligand have been found. See, e.g., Table 3. Thus, differential splicing of message may lead to membrane bound forms, soluble forms, and modified versions of ligand.

Structural studies of the ligands will lead to design of new ligands, particularly analogues exhibiting agonist or antagonist properties on the receptor. This can be combined with previously described screening methods to isolate ligands exhibiting desired spectra of activities.

Expression in other cell types will often result in glycosylation differences in a particular ligand. Various species variants may exhibit distinct functions based upon structural differences other than amino acid sequence. Differential modifications may be responsible for differential function, and elucidation of the effects are now made possible.

Thus, the present invention provides important reagents related to a physiological ligand-receptor interaction. Although the foregoing description has focused primarily upon the mouse Flt3 ligand, those of skill in the art will immediately recognize that the invention encompasses other ligands, e.g., rat and other mammalian species or allelic variants, as well as variants thereof.

V. Antibodies

Antibodies can be raised to various Flt3 ligands, including species or allelic variants, and fragments thereof, both in their naturally occurring forms and in their recombinant forms. Additionally, antibodies can be raised to Flt3 ligands in either their active forms or in their inactive forms. Anti-idiotypic antibodies are also contemplated.

Antibodies, including binding fragments and single chain versions, against predetermined fragments of the ligands can be raised by immunization of animals with conjugates of the fragments with immunogenic proteins. Monoclonal antibodies are prepared from cells secreting the desired antibody. These antibodies can be screened for binding to normal or defective Flt3 ligands, or screened for agonistic or antagonistic activity, e.g., mediated through the receptor. These monoclonal antibodies will usually bind with at least a $K_D$ of about 1 mM, more usually at least about 300 µm, typically at least about 10 µM, more typically at least about 30 µM, preferably at least about 10 µM, and more preferably at least about 3 µM or better.

The antibodies, including antigen binding fragments, of this invention can have significant diagnostic or therapeutic value. They can be potent antagonists that bind to the receptor and inhibit ligand binding or inhibit the ability of a ligand to elicit a biological response. They also can be useful as non-neutralizing antibodies and can be coupled to toxins or radionuclides so that when the antibody binds to ligand, a cell expressing it, e.g., on its surface, is killed. Further, these antibodies can be conjugated to drugs or other therapeutic agents, either directly or indirectly by means of a linker, and may effect drug targeting.

The antibodies of this invention can also be useful in diagnostic applications. As capture or non-neutralizing antibodies, they can be screened for ability to bind to the ligands without inhibiting receptor binding. As neutralizing antibodies, they can be useful in competitive binding assays. They will also be useful in detecting or quantifying Flt3 ligand or its receptors.

Ligand fragments may be joined to other materials, particularly polypeptides, as fused or covalently joined polypeptides to be used as immunogens. A ligand and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York, and Williams, et al. (1967) *Methods in Immunology and Immunochemistry*, Vol. 1, Academic Press, New York, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256:495-497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275-1281; and Ward, et al. (1989) *Nature* 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified Flt3 ligand protein will be released.

The antibodies may also be used to screen expression libraries for particular expression products. Usually the antibodies used in such a procedure will be labeled with a moiety allowing easy detection of presence of antigen by antibody binding.

Antibodies raised against each Flt3 ligand will also be useful to raise anti-idiotypic antibodies. These will be useful in detecting or diagnosing various immunological conditions related to expression of the respective antigens.

VI. Nucleic Acids

The described peptide sequences and the related reagents are useful in isolating a DNA clone encoding Flt3 ligand, e.g., from a natural source. Typically, it will be useful in isolating a gene from mouse, and similar procedures will be applied to isolate genes from other species, e.g., warm blooded animals, such as birds and mammals. See Table 3. Cross hybridization will allow isolation of ligand from other species. A number of different approaches should be available to successfully isolate a suitable nucleic acid clone.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual Cold Spring Harbor Press.* Alternatively, the *Flt*3 receptor can be used as a specific binding reagent, and advantage can be taken of its specificity of binding, much like an antibody would be used.

For example, the specific binding composition could be used for screening of an expression library made from a cell line which expresses a Flt3 ligand. The screening can be standard staining of surface expressed ligand, or by panning. Screening of intracellular expression can also be performed by various staining or immunofluorescence procedures. The binding compositions could be used to affinity purify or sort out cells expressing the ligand.

The peptide segments can also be used to predict appropriate oligonucleotides to screen a library. The genetic code can be used to select appropriate oligonucleotides useful as probes for screening. See, e.g., Table 3. In combination with polymerase chain reaction (PCR) techniques, synthetic oligonucleotides will be useful in selecting correct clones from a library. Complementary sequences will also be used as probes or primers. Based upon identification of the likely amino terminus, the third peptide should be particularly useful, e.g., coupled with anchored vector or poly-A complementary PCR techniques or with complementary DNA of other peptides. Peptide 2 of Table 3 was originally assigned the sequence D Y P V T V A V ( ) L Q (D).

TABLE 3

Flt3 ligand peptide sequences and exemplary predicted
oligonucleotide probes/primers. Also can use complementary sequences.

```
1.      F       V       Q       T       (NCST)       I       (S)  (H)  L L       K
a)     TT(T/C) GTN CA(G/A) ACN AA(C/T) AT(A/C/T)
b)     TT(T/C) GTN CA(G/A) ACN TG(T/C) AT(A/C/T)
c)     TT(T/C) GTN CA(G/A) ACN AG(C/T) AT(A/C/T)
d)     TT(T/C) GTN CA(G/A) ACN TCN     AT(A/C/T)
e)     TT(T/C) GTN CA(G/A) ACN ACN     AT(A/C/T) (see SEQ ID NO: 18-22)

2.      D       Y       P       V       T       V       A       V (N) L Q (D) E
       GA(T/C) TA(T/C) CCN GTN ACN GTN (see SEQ ID NO: 23)

3.      T       P       D       C       Y       F       S H S
       ACN CCN GA(T/C) TG(T/C) TA(T/C) TT(T/C) (see SEQ ID NO: 24)

4.      W       I       E       Q       L       K       (Q) (P) (G) (S)
a)     TGG AT(A/C/T) GA(G/A) CA(G/A) CTN     AA(G/A)
b)     TGG AT(A/C/T) GA(G/A) CA(G/A) TT(A/G) AA(G/A) (see SEQ ID NO: 25-26)

5.      N       F       K       V       K       F
       AA(T/C) TT(T/C) AA(A/G) GTN AA(A/G) TT(T/C) (see SEQ ID NO: 27)

and sequence:
       ACT CCT GAC TGT TAC TTC AGC CAC AGT CCC ATC TCC TCC AAC TTC AAA GTG
AAG TTT AGA GAG TTG ACT GAC CAC CTG CTT AAA GAT (see SEQ ID NO: 28)

sequences of various mammalian Flt3 ligand variants are:

mouse T110/MB8/T118 common sequence to Pro 163 (see SEQ ID NO: 37-38, 41-42, and 39-40)

GAATTCGCGGCCGCGTCGAGCCTGGCGGGACTGAGCCCGAGACCTGCCCTCCTGTC

ACTTCCAAGAACCTGTCACAGGCATGAGGGGTCCCCGGCAGAG ATG ACA GTG CTG GCG CCA
                                            MET Thr Val Leu Ala Pro      6

GCC TGG AGC CCA AAT TCC TCC CTG TTG CTG CTG TTG CTG CTG CTG AGT CCT
Ala Trp Ser Pro Asn Ser Ser Leu Leu Leu Leu Leu Leu Leu Leu Ser Pro     23

TGC CTG CGG GGG ACA CCT GAC TGT TAC TTC AGC CAC AGT CCC ATC TCC TCC
Cys Leu Arg Gly Thr Pro Asp Cys Tyr Phe Ser His Ser Pro Ile Ser Ser     40

AAC TTC AAA GTG AAG TTT AGA GAG TTG ACT GAC CAC CTG CTT AAA GAT TAC
Asn Phe Lys Val Lys Phe Arg Glu Leu Thr Asp His Leu Leu Lys Asp Tyr     57

CCA GTC ACT GTG GCC GTC AAT CTT CAG GAC GAG AAG CAC TGC AAG GCC TTG
Pro Val Thr Val Ala Val Asn Leu Gln Asp Glu Lys His Cys Lys Ala Leu
Pro Val Thr Val Ala Val Asn Leu Gln Asp Glu      74

TGG AGC CTC TTC CTA GCC CAG CGC TGG ATA GAG CAA CTG AAG ACT GTG GCA
Trp Ser Leu Phe Leu Ala Gln Arg Trp Ile Glu Gln Leu Lys Thr Val Ala     91

GGG TCT AAG ATG CAA ACG CTT CTG GAG GAC GTC AAC ACC GAG ATA CAT TTT
Gly Ser Lys Met Gln Thr Leu Leu Glu Asp Val Asn Thr Glu Ile His Phe    108

GTC ACC TCA TGT ACC TTC CAG CCC CTA CCA GAA TGT CTG CGA TTC GTC CAG
Val Thr Ser Cys Thr Phe Gln Pro Leu Pro Glu Cys Leu Arg Phe Val Gln    125

ACC AAC ATC TCC CAC CTC CTG AAG GAC ACC TGC ACA CAG CTG CTT GCT CTG
Thr Asn Ile Ser His Leu Leu Lys Asp Thr Cys Thr Gln Leu Leu Ala Leu    142

AAG CCC TGT ATC GGG AAG GCC TGC CAG AAT TTC TCT CGG TGC CTG GAG GTG
Lys Pro Cys Ile Gly Lys Ala Cys Gln Asn Phe Ser Arg Cys Leu Glu Val    159

T110
CAG TGC CAG CCG Δ GAC TCC TCC ACC CTG CTG CCC CCA AGG AGT CCC ATA GCC
Gln Cys Gln Pro Δ Asp Ser Ser Thr Leu Leu Pro Pro Arg Ser Pro Ile Ala  176
```

TABLE 3-continued

Flt3 ligand peptide sequences and exemplary predicted oligonucleotide probes/primers. Also can use complementary sequences.

```
CTA GAA GCC ACG GAG CTC CCA GAG CCT CGG CCC AGG CAG CTG TTG CTC CTG
Leu Glu Ala Thr Glu Leu Pro Glu Pro Arg Pro Arg Gln Leu Leu Leu Leu    193

CTG CTG CTG CTG CTG CCT CTC ACA CTG GTG CTG CTG GCA GCC GCC TGG GGC
Leu Leu Leu Leu Leu Pro Leu Thr Leu Val Leu Leu Ala Ala Ala Trp Gly    210

CTT CGC TGG CAA AGG GCA AGA AGG AGG GGG GAG CTC CAC CCT GGG GTG CCC
Leu Arg Trp Gln Arg Ala Arg Arg Arg Gly Glu Leu His Pro Gly Val Pro    227

CTC CCC TCC CAT CCC TAGGATGCGAGCCTTGTGCATCGTTGACTCAGCCAGGGTCTTATCTC
Leu Pro Ser His Pro                                                    232

GAGTTGGGAACCAAAACAAGGAACAAGCTAGGCAAGTGCTGTGCTGAGTTACATCCCCAGCCCAGAG
GACACACTGTCTGGGTATGGCGATGGACACTGTAATTCCAGTGCTTCTGGATTGGACATGCTGAAAC
TGGATACTGACTTTAAGAAAAACAGAAAGGAAGAACCCCCC

MB8 into T110 sequence insert (29 amino acids)
  [TGC CAG CCG] GAT AGG GTC TCA TTA TTA TGC AGG CTA GGC CTG ACC CTG
       ...     Asp Arg Val Ser Leu Leu Cys Arg Leu Gly Leu Thr Leu     Δ13

AAC TCA AAG CAA TCC TCC TGC CTC AGT GTC CTG AGT GCT GGG ATT ACA [GAC TCC]
Asn Ser Lys Gln Ser Ser Cys Leu Ser Val Leu Ser Ala Gly Ile Thr ...    Δ29 or T118, which diverges from the common sequence at the position
        designated by Δ after Pro 163
        ... GGT AAC GGT GGC CCC AGA GCC CAG CAC CAT GGT GCC ACC
        ... Gly Asn Gly Gly Pro Arg Ala Gln His His Gly Ala Thr        176

AGG CTC ACA GCC ACA GCC TTG CTA ACT GTG TGT CCA GGG CTT CTG CTC CCA
Arg Leu Thr Ala Thr Ala Leu Leu Thr Val Cys Pro Gly Leu Leu Leu Pro    193

CTA GTT GGC ACT TCA CAC ATG TTC TTT CTC CCT TAT TTT CTC TCT TTT CTT
Leu Val Gly Thr Ser His Met Phe Phe Leu Pro Tyr Phe Leu Ser Phe Leu    210

TCT TCT TTT TTA AAG ATG TAT CTT TAT GTG.TGAGTGTTTTACCTACATGCCTGTAAG
Ser Ser Phe Leu Lys Met Tyr Leu Tyr Val                                220

TGCACTGAATGTGTGTCTGGTGCCTGCAGAGGCCAGAAGAGGGCACCAGATCCCCTGAAACTGGAGT
CTCTNNGCTCCGTGTGAACCACCACGTGGTGCTGGGACCCAGGTCCAATGCAAGAGCACCCAGGGTT
CTTACCTGGCTGA human S86/S109 common sequence to Pro 160 (see SEQ ID NO: 33-34 and 35-36)
             GAAAGGGCTGTCACCCGGCTTGGCCCCTTCCACACCCAACTGGGGCAAGCC TGACCCGGCGACAGGAGGCATGAGGGGCCCCCGGCCGAA ATG ACA GTG CTG GCG CCA GCC
                                        MET Thr Val Leu Ala Pro Ala     7

TGG AGC CCA ACA ACC TAT CTC CTC CTG CTG CTG CTG AGC TCG GGA CTC
Trp Ser Pro Thr Thr Tyr Leu Leu Leu Leu Leu Leu Ser Ser Gly Leu         24

AGT GGG ACC CAG GAC TGC TCC TTC CAA CAC AGC CCC ATC TCC TCC GAC TTC
Ser Gly Thr Gln Asp Cys Ser Phe Gln His Ser Pro Ile Ser Ser Asp Phe    41

GCT GTC AAA ATC CGT GAG CTG TCT GAC TAC CTG CTT CAA GAT TAC CCA CTC
Ala Val Lys Ile Arg Glu Leu Ser Asp Tyr Leu Leu Gln Asp Tyr Pro Val    58
                                 #
ACC GTG GCC TCC AAC CTG CAG GAC GAG GAG CTC TGC GGG GCG CTC TGG CGG
Thr Val Ala Ser Asn Leu Gln Asp Glu Glu Leu Gys Gly Ala Leu Trp Arg    75

CTG GTC CTG GCA CAG CGC TGG ATG GAG CGG CTC AAG ACT GTC GCT GGG TCC
Leu Val Leu Ala Gln Arg Trp Met Glu Arg Leu Lys Thr Val Ala Gly Ser    92

AAG ATG CAA GGC TTG CTG GAG CGC GTG AAC ACG GAG ATA CAC TTT GTC ACC
Lys Met Gln Gly Leu Leu Glu Arg Val Asn Thr Glu Ile His Phe Val Thr    109

AAA TGT GCC TTT CAG CCC CCC CCC AGC TGT CTT CGC TTC GTC CAG ACC AAC
Lys Cys Ala Phe Gln Pro Pro Pro Ser Cys Leu Arg Phe Val Gln Thr Asn    126

ATC TCC CGC CTC CTG CAG GAG ACC TCC GAG CAG CTG GTG GCG CTG AAG CCC
Ile Ser Arg Leu Leu Gln Glu Thr Ser Glu Gln Leu Val Ala Leu Lys Pro    143

TGG ATC ACT CGC CAG AAC TTC TCC CGG TGC CTG GAG CTG CAG TGT CAG CCC
Trp Ile Thr Arg Gln Asn Phe Ser Arg Gys Leu Glu Leu Gln Cys Gln Pro    160
```

TABLE 3-continued

Flt3 ligand peptide sequences and exemplary predicted
oligonucleotide probes/primers. Also can use complementary sequences.

```
S86, continuing from Pro 160 of the common sequence
GAC TCC TCA ACC CTG CCA CCC CCA TGG AGT CCC CGG CCC CTG GAG GCC ACA
Asp Ser Ser Thr Leu Pro Pro Pro Trp Ser Pro Arg Pro Leu Glu Ala Thr    177

GCC CCG ACA GCC CCG CAG CCC CCT CTG CTC CTC CTA CTG CTG CTG CCC GTG
Ala Pro Thr Ala Pro Gln Pro Pro Leu Leu Leu Leu Leu Leu Leu Pro Val    194

GGC CTC CTG CTG CTG GCC GCT GCC TGG TGC CTG CAC TGG CAG AGG ACG CGG
Gly Leu Leu Leu Leu Ala Ala Ala Trp Cys Leu His Trp Gln Arg Thr Arg    211

CGG AGG ACA CCC CGC CCT GGG GAG CAG GTG CCC CCC GTC CCC AGT CCC CAG
Arg Arg Thr Pro Arg Pro Gly Glu Gln Val Pro Pro Val Pro Ser Pro Gln    228

GAC CTG CTG CTT GTG GAG CAC TGACCTGGCCAAGGCCTCATCCTGGGGAGGATACGTAGG
Asp Leu Leu Leu Val Glu His                                            235

CACACAGAGGGGAGTCACCAGCC or S109, continuing from Pro 160 of the common sequence
GGT GCC CCC CGT CCC CAG TCC CCA GGA CCT GCT GCT TGT GGA GCA CTG ACC
Gly Ala Pro Arg Pro Gln Ser Pro Gly Pro Ala Ala Cys Gly Ala Leu Thr    177

TGG CCA AGG CCT CAT CCT GGG GAG GAT ACT GAG GCA CAC AGA GGG GAG TCA
Trp Pro Arg Pro His Pro Gly Glu Asp Thr Glu Ala His Arg Gly Glu Ser    194

CCA GCC AGA GGA TGC ATA GCC TGG ACA CAG AGG AAG TTG GCT AGA GGC CGG
Pro Ala Arg Gly Cys Ile Ala Trp Thr Gln Arg Lys Leu Ala Arg Gly Arg    211

TCC CTT CCT TGG GCC CCT CTC ATT CCC TCC CCA GAA TGG AGG CAA CGC CAG
Ser Leu Pro Trp Ala Pro Leu Ile Pro Ser Pro Glu Trp Arg Gln Arg Gln    228

AAT CCA GCA CCG GCC CCA TTT ACC CAA CTC TGT ACA AAG CCC TTG TCC CCA
Asn Pro Ala Pro Ala Pro Phe Thr Gln Leu Cys Thr Lys Pro Leu Ser Pro    245

TGAAATTGTATATAAATCATCCTTTTCTACCAAAAAAAAAAAAAAA
```

An isolated nucleic acid encoding an amino terminal segment has been isolated and sequenced and provides the following sequence: ACT CCT GAC TGT TAC TTC AGC CAC AGT CCC ATC, TCC TCC AAC TTC AAA GTG AAG TTT AGA GAG TTG ACT GAC CAC CTG CTT AAA GAT. This may be used as a probe to isolate a longer or full length clone and will lead to isolation of other species or allelic variants or other closely related genes. See Table 5, below, and Table 3.

This invention contemplates use of isolated DNA or fragments to encode a biologically active corresponding Flt3 ligand polypeptide. In addition, this invention covers isolated or recombinant DNA which encodes a biologically active protein or polypeptide which is capable of hybridizing under appropriate conditions with the DNA sequences described herein. Said biologically active protein or polypeptide can be an intact ligand, or fragment, and have an amino acid sequence as disclosed in Table 1. Further, this invention covers the use of isolated or recombinant DNA, or fragments thereof, which encode proteins which are homologous to a Flt3 ligand or which was isolated using cDNA encoding a Flt3 ligand as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

A DNA which codes for a Flt3 ligand protein will be particularly useful to identify genes, mRNA, and cDNA species which code for related or homologous ligands, as well as DNAs which code for homologous proteins from different species. There are likely homologues in other species, including primates. Various Flt3 ligand proteins should be homologous and are encompassed herein. However, even proteins that have a more distant evolutionary relationship to the ligand can readily be isolated under appropriate conditions using these sequences if they are sufficiently homologous. Primate Flt3 ligand proteins are of particular interest.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502-1504; Travis (1992) *Science* 256:1392-1394; Kuhn, et al. (1991) *Science* 254:707-710; Capecchi (1989) *Science* 244:1288; Robertson (1987) (ed.) *Teratocarcinomas and Embryonic Stem Cells: A Practical Approach* IRL Press, Oxford; and Rosenberg (1992) *J. Clinical Oncology* 10:180-199.

Homologous nucleic acid sequences, when compared, exhibit significant similarity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence derived from Table 2.

Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, Kanehisa (1984) *Nuc. Acids Res.* 12:203-213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349-370.

Flt3 ligand from other mammalian species can be cloned and isolated by cross-species hybridization of closely related species. See, e.g., below. Homology may be relatively low between distantly related species, and thus hybridization of relatively closely related species is advisable. Alternatively, preparation of an antibody preparation which exhibits less species specificity may be useful in expression cloning approaches.

VII. Making Flt3 Ligand; Mimetics

DNA which encodes the Flt3 ligand or fragments thereof can be obtained by chemical synthesis, screening cDNA libraries, or by screening genomic libraries prepared from a wide variety of cell lines or tissue samples.

This DNA can be expressed in a wide variety of host cells for the synthesis of a full-length ligand or fragments which can in turn, for example, be used to generate polyclonal or monoclonal antibodies; for binding studies; for construction and expression of modified molecules; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encodes a Flt3 ligand, or a fragment thereof, typically encoding a biologically active polypeptide. The DNA can be under the control of a viral promoter and can encode a selection marker. This invention further contemplates use of such expression vectors which are capable of expressing eukaryotic cDNA coding for a Flt3 ligand in a prokaryotic or eukaryotic host, where the vector is compatible with the host and where the eukaryotic cDNA coding for the ligand is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the ligand or its fragments in various hosts using vectors that do not contain a replication origin that is recognized by the host cell. It is also possible to use vectors that cause integration of a Flt3 ligand gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (1988) (eds.) *Vectors: A Survey of Molecular Cloning Vectors and Their Uses*, Buttersworth, Boston, Mass.

Transformed cells include cells, preferably mammalian, that have been transformed or transfected with Flt3 ligand gene containing vectors constructed using recombinant DNA techniques. Transformed host cells usually express the ligand or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the Flt3 ligands or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses*, Buttersworth, Boston, Chapter 10, pp. 205-236.

Lower eukaryotes, e.g., yeasts and *Dictyostelium*, may be transformed with Flt3 ligand sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active Flt3 ligand protein. In principle, any higher eukaryotic tissue culture cell line is workable, e.g., insect baculovirus expression systems, whether from an invertebrate or vertebrate source. However, mammalian cells are preferred, in that the processing, both cotranslationally and posttranslationally. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell. Biol.* 5:1136-

1142; pMc1neo Poly-A, see Thomas, et al. (1987) *Cell* 51:503-512; and a baculovirus vector such as pAC 373 or pAC 610.

It will often be desired to express a Flt3 ligand polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the Flt3 ligand gene may be co-transformed with one or more genes encoding mammalian or other glycosylating enzymes. Using this approach, certain mammalian glycosylation patterns will be achievable or approximated in prokaryote or other cells.

The Flt3 ligand, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim, Biophys, Acta* 988:427-454; Tse, et al. (1985) *Science* 230:1003-1008; and Brunner, et al. (1991) *J. Cell Biol.* 114:1275-1283.

Now that the Flt3 ligand has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The Flt3 ligand, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149-2156.

The prepared ligand and fragments thereof can be isolated and purified from the reaction mixture by means of peptide separation, for example, by extraction, precipitation, electrophoresis and various forms of chromatography, and the like. The Flt3 ligands of this invention can be obtained in varying degrees of purity depending upon its desired use. Purification can be accomplished by use of the protein purification techniques disclosed herein or by the use of the antibodies herein described in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the ligand, or lysates or supernatants of cells producing the Flt3 ligand as a result of DNA techniques, see below.

VIII. Uses

The present invention provides reagents which will find use in diagnostic applications as described elsewhere herein, e.g., in the general description for developmental abnormalities, or below in the description of kits for diagnosis.

This invention also provides reagents with significant therapeutic value. The Flt3 ligand (naturally occurring or recombinant), fragments thereof and antibodies thereto, along with compounds identified as having binding affinity to Flt3 ligand, should be useful in the treatment of conditions associated with abnormal physiology or development, including abnormal proliferation, e.g., cancerous conditions, or degenerative conditions. In particular, modulation of development of lymphoid cells is likely, but the wider tissue distribution on non-lymphoid tissues, e.g., gonads and neural cells, suggests that development of those tissues will be similarly responsive. Abnormal proliferation, regeneration, degeneration, and atrophy may be modulated by appropriate therapeutic treatment using the compositions provided herein. For example, a disease or disorder associated with abnormal expression or abnormal signaling by a Flt3 ligand should be a likely target for an agonist or antagonist of the ligand. The ligand likely plays a role in regulation or development of hematopoietic cells, e.g., lymphoid cells, which affect immunological responses, e.g., autoimmune disorders.

Other abnormal developmental conditions are known in each of the cell types shown to possess Flt3 receptor mRNA by Northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. For example, neural and brain abnormalities exist in, e.g., cerebrovascular disease, CNS neoplasms, demyelinating diseases, and muscular dystrophies. Liver disorders, kidney disorders, cardiopulmonary disorders, and other problems often cause medical symptoms. These problems may be susceptible to prevention or treatment using compositions provided herein.

Recombinant Flt3 or Flt3 ligand antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using Flt3 receptor or fragments thereof can be performed to identify compounds having binding affinity to Flt3 ligand, including isolation of associated components. Subsequent biological assays can then be utilized to determine if the compound has intrinsic stimulating activity and is therefore a blocker or antagonist in that it blocks the activity of the ligand. Likewise, a compound having intrinsic stimulating activity can activate the receptor and is thus an agonist in that it simulates the activity of Flt3 ligand. This invention further contemplates the therapeutic use of antibodies to Flt3 ligand as antagonists. This approach should be particularly useful with other Flt3 ligand species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage various considerations are described, e.g., in Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 μm concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

Flt3 ligand, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; Avis, et al. (eds.) (1993) *Pharmaceutical Dosage Forms: Parenteral Medications* Dekker, New York; Lieberman, et al. (eds.) (1990) *Pharmaceutical Dosage Forms: Tablets* Dekker, New York; and Lieberman, et al. (eds.) (1990) *Pharmaceutical Dosage Forms: Disperse Systems* Dekker, New York. The therapy of this invention may be combined with or used in association with other chemotherapeutic or chemopreventive agents.

Both the naturally occurring and the recombinant form of the Flt3 ligands of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767-773, which describes means for testing of binding affinity by a plurality of defined polymers synthesized on a solid substrate. The development of suitable assays can be greatly facilitated by the availability of large amounts of purified, soluble Flt3 ligand as provided by this invention.

For example, antagonists can normally be found once the ligand has been structurally defined. Testing of potential ligand analogues is now possible upon the development of highly automated assay methods using a purified Flt3 receptor. In particular, new agonists and antagonists will be discovered by using screening techniques described herein. Of particular importance are compounds found to have a combined binding affinity for multiple Flt3 receptors, e.g., compounds which can serve as antagonists for species variants of Flt3 ligand.

This invention is particularly useful for screening compounds by using recombinant receptor in any of a variety of drug screening techniques. The advantages of using a recombinant protein in screening for specific ligands include: (a) improved renewable source of the Flt3 receptor from a specific source; (b) potentially greater number of ligands per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing the Flt3 receptor. Cells may be isolated which express a receptor in isolation from any others. Such cells, either in viable or fixed form, can be used for standard ligand/receptor binding assays. See also, Parce, et al. (1989) *Science* 246:243-247; and Owicki, et al. (1990) *Proc. Nat'l Acad. Sci. USA* 87:4007-4011, which describe sensitive methods to detect cellular responses. Competitive assays are particularly useful, where the cells (source of Flt3 ligand) are contacted and incubated with a labeled receptor or antibody having known binding affinity to the ligand, such as $^{125}$I-antibody, and a test sample whose binding affinity to the binding composition is being measured. The bound and free labeled binding compositions are then separated to assess the degree of ligand binding. The amount of test compound bound is inversely proportional to the amount of labeled receptor binding to the known source. Any one of numerous techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on Flt3 ligand mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of the Flt3 ligand. These cells are stably transformed with DNA vectors directing the expression of a Flt3 ligand, e.g., an engineered membrane bound form. Essentially, the membranes would be prepared from the cells and used in any receptor/ligand binding assay such as the competitive assay set forth above.

Still another approach is to use solubilized, unpurified or solubilized, purified Flt3 ligand from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to Flt3 receptor and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified Flt3 receptor, and washed. The next step involves detecting bound Flt3 receptor.

Rational drug design may also be based upon structural studies of the molecular shapes of the Flt3 ligand and other effectors or analogues. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

Purified Flt3 ligand can be coated directly onto plates for use in the aforementioned drug screening techniques. However, non-neutralizing antibodies to these ligands can be used as capture antibodies to immobilize the respective ligand on the solid phase.

IX. Kits

This invention also contemplates use of Flt3 ligand proteins, fragments thereof, peptides, and their fusion products in a variety of diagnostic kits and methods for detecting the presence of ligand or a Flt3 receptor. Typically the kit will have a compartment containing either a defined Flt3 ligand peptide or gene segment or a reagent which recognizes one or the other, e.g., receptor fragments or antibodies.

A kit for determining the binding affinity of a test compound to a Flt3 ligand would typically comprise a test compound; a labeled compound, for example a receptor or antibody having known binding affinity for the ligand; a source of Flt3 ligand (naturally occurring or recombinant); and a means for separating bound from free labeled compound, such as a solid phase for immobilizing the ligand. Once compounds are screened, those having suitable binding affinity to the ligand can be evaluated in suitable biological assays, as are well known in the art, to determine whether they act as agonists or antagonists to the receptor. The availability of recombinant Flt3 ligand polypeptides also provide well defined standards for calibrating such assays.

A preferred kit for determining the concentration of, for example, a Flt3 ligand in a sample would typically comprise a labeled compound, e.g., receptor or antibody, having known binding affinity for the ligand, a source of ligand (naturally occurring or recombinant) and a means for separating the bound from free labeled compound, for example, a solid phase for immobilizing the Flt3 ligand. Compartments containing reagents, and instructions, will normally be provided.

Antibodies, including antigen binding fragments, specific for the Flt3 ligand or ligand fragments are useful in diagnostic applications to detect the presence of elevated levels of Flt3 ligand and/or its fragments. Such diagnostic assays can employ lysates, live cells, fixed cells, immunofluorescence, cell cultures, body fluids, and further can involve the detection of antigens related to the ligand in serum, or the like.

Diagnostic assays may be homogeneous (without a separation step between free reagent and antigen-ligand complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SL-FIA), and the like. For example, unlabeled antibodies can be employed by using a second antibody which is labeled and which recognizes the antibody to a Flt3 ligand or to a particular fragment thereof. Similar assays have also been extensively discussed in the literature. See, e.g., Harlow and Lane (1988) *Antibodies: A Laboratory Manual*, CSH.

Anti-idiotypic antibodies may have similar use to diagnose presence of antibodies against a Flt3 ligand, as such may be diagnostic of various abnormal states. For example, overproduction of Flt3 ligand may result in production of various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or receptor, or labeled Flt3 ligand is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the ligand, test compound, Flt3 ligand, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. The Flt3 ligand can be immobilized on various matrixes followed by washing. Suitable matrixes include plastic such as an ELISA plate, filters, and beads. Methods of immobilizing the Flt3 ligand to a matrix include, without limitation, direct adhesion to plastic, use of a capture antibody, chemical coupling, and biotin-avidin. The last step in this approach involves the precipitation of ligand/receptor or ligand/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457-1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a Flt3 ligand. These sequences can be used as probes for detecting levels of the ligand message in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89-97.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning A Laboratory Manual*, Cold Spring Harbor Laboratory, Cold Spring Harbor Press; Sambrook, et al. (1989) *Molecular Cloning: A Laboratory Manual*, (2d ed.), vols 1-3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York; Innis, et al. (eds.) (1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, N.Y.; and Crowe, et al. (1992) *OIAexpress: The High Level Expression & Protein Purification System* QUIAGEN, Inc., Chatsworth, Calif.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

Additional description has been published after the priority date of the description of this ligand in Hannum, et al. (1994) *Nature* 368:643-648, which is incorporated herein by reference for all purposes.

II. Production and Sequencing of the Flt3 Ligand

Assays for the Flt3/Flk2 Ligand

Baf3 cells (mouse pre-B cell line; see Palacios, et al. ($L_{985}$) *Cell* 41:727-734; and Palacios, et al. (1984) *Nature* 309:126-131) were stably transfected with the cDNA for the Flt3 receptor, Rosnet, et al. (1991) *Oncogene* 6:1641-1650. Two methods were used to observe the response of these cells to samples containing the ligand. The main assay is an MTT assay in which the Flt3-transfected cells (Baflts) survive a 24-hour incubation in the presence of the ligand (but not if the ligand is absent) and can then take up and cleave the MTT dye. See Mosmann (1983) *J. Immunol. Methods* 65:55-63. Untransfected Baf cells die both in the presence and absence of the ligand, and samples are therefore routinely assayed in parallel on both cell types. The difference in signal obtained from these two cell types (Baflt-Baf) is a measure of the amount of ligand present in a sample.

In some cases where active samples also contain substances that are toxic to the cells, the MTT assay with Baflts can fail to detect the presence of the ligand. A second method for detecting the ligand in these cases is to take advantage of the fact that receptors such as c-fms, c-kit, and flt-3 rapidly (within 5 minutes) auto-phosphorylate themselves while binding their appropriate ligands. This response is much less sensitive to toxic substances than is the 24-hour MTT assay. Auto-phosphorylated receptor is observed by lysing the responder cells with detergent, e.g., NP-40, immunoprecipitating Flt3 using antibodies directed against the intracellular portion of the molecule, and separating the immunoprecipitate on SDS-PAGE, blotting to nitrocellulose, probing with an anti-phosphotyrosine monoclonal antibody, and detecting phosphotyrosine, e.g., with a horseradish peroxidase-linked anti-immunoglobulin and developing with a chemiluminescent substrate.

More specifically, to measure Flt3 ligand biological activity, MTT colorimetric assays, according to Mosmann, et al. (1983) *J. Immunol. Methods* 65:55-63, were performed in parallel on Ba/F3 and Baflt cells using $10^4$ cells/well over a 20 hr incubation. The Flt3 ligand-specific dose-response was calculated by subtracting the Ba/F3 titration signals from the corresponding Baflt titration signals. A unit of Flt3 ligand activity is defined as the amount of active material required to produce 50% maximal stimulation under these conditions. Flt3 ligand activity was also detected by a receptor phosphorylation assay. $3\times10^6$ Baflt or Ba/F3 cells were stimulated with ligand for five minutes. Cell lysates were prepared and immunoprecipitated with an antiserum directed against the kinase insert domain of Flt3/Flk2. This antiserum was also used to detect the chimeric c-fms/Flt3 receptor on Raff-8 cells. The immunoprecipitates were run on SDS-PAGE, and the gels were electroblotted onto a PVDF membrane. The filter was probed with an antiphosphotyrosine antibody (4G10).

Source of the Flt3 Ligand

Multiple cell lines were screened for one which expresses a Flt3 ligand. A mouse thymic stromal cell line TA4 (provided by Donna Rennick, DNAX Research Institute) was selected for its ease in handling for large scale production. Cells were grown on roller bottles and 7 day-conditioned media supernatants (serum-free) were harvested, passed through 0.22 µm filters, concentrated 100-fold, and stored frozen at −80° C. The Baflt bioassay applied to a panel of mouse and human stromal cell lines was screened for Flt3 ligand activity; nearly all of them were positive including a human stromal cell line, SV48, suggesting that human Flt3 ligand can function with the mouse receptor.

Biochemical Characterization of the Flt3 Ligand.

The Flt3 ligand activity has been defined by its separation parameters using different protein separation techniques. However, because of low expression levels, the detection of the activity was greatly facilitated by the concentration of the media. Aliquots of 100× concentrated TA4 cell supernatant, typically representing 10 L of crude supernatant, were subjected to various biochemical purification techniques including ammonium sulfate precipitation, hydrophobic interaction chromatography, anion and cation exchange chromatographies, gel filtration chromatography, and reversed phase chromatography. See Table 2. The behavior of the biological activity representing the Flt3 ligand in each of these techniques is summarized below:

Ammonium Sulfate precipitation (at 4° C.): activity found in 60-85% saturated $(NH_4)_2SO_4$ pellet;

Hydrophobic Interaction Chromatography [$(NH_4)_2SO_4$ gradient in 20 mM Tris, pH 7.5 on a Phenyl-5PW column]: activity eluted between 900-750 mM $(NH_4)_2SO_4$;

Anion Exchange Chromatography (NaCl gradient in 20 mM Tris, pH 7.5 on Mono Q column): activity eluted between 130-250 mM NaCl;

Cation Exchange Chromatography (NaCl gradient in 10 mM citrate, pH 3.0 on Mono S column): the bulk of the activity eluted between 440-540 mM NaCl;

Gel Filtration (Sephacryl S200 column): the activity ran with an apparent molecular weight of 70 kD;

Reversed Phase HPLC (water to acetonitrile gradient in 0.1% TFA on a Poros R/H column): the activity eluted between 32-35% acetonitrile.

Engineering, Production, and Purification of Soluble Flt3.

A soluble fragment of the Flt3 receptor was constructed by removing the membrane spanning and cytoplasmic domains of the Flt3 receptor, fused to a sequence, e.g., FLAG, useful for purifying the expression product of the construct. See, e.g., Crowe, et al. (1992) *OTAexpress: The High Level Expression & Protein Purification System* QUIAGEN, Inc. Chatsworth, Calif.; and Hopp, et al. (1988) *Bio/Technology* 6:1204-1210. To purify Flt3 ligand, a recombinant form of the receptor composed of the extracellular domain of mouse Flt3/Flk2 was expressed in insect cells, purified, and attached to beads. The construct allows for efficient affinity purification of the soluble product. Appropriate secretion or processing sites may also be engineered into the construct by standard methods. Purification may be achieved by use of affinity purification, e.g., antibodies against the receptor, or by standard protein purification methods. Typically, the affinity reagents or purification procedures can be performed using recombinant receptor.

More specifically, two tags were engineered to the carboxy terminus of the extracellular domain of the Flt3 receptor. pMEXneo-Flt3 was used as a source to modify the Flt3 cDNA to introduce a BglII site at nucleotide 1662, directly following Ser544, the last amino acid of the extracellular domain. An XmaI/BglII fragment containing the entire extracellular Flt3 domain was cloned into pHFBg1, a derivative of pVL1393 from Invitrogen Corp. The pHFBg1 contains a $His_6$-FLAG-stop codon sequence fused in frame with the BglII site of the polylinker. See Table 4. The resulting plasmid was named pHF/Flt3.

TABLE 4

Relevant portion of soluble Flt3 receptor construct
See SEQ ID NO: 29-30.

```
    Xma I
    Sma I                            Not I
   BamHI       XbaI  EcoRI        XmaIIIPstIBglII
5' GGATCCCGGGTACCTTCTAGAATTCCGGAGCGGCCGCTGCAGATCT-
3' CCTAGGGCCCATGGAAGATCTTAAGGCCTCGCCGGCGACGTCTAGA-
    AspProGlyTyrLeuLeuGluPheArgSerGlyArgCysArgSer

CATCACCATCACCATCACGATTACAAGGACGATGACGATAAG-
GTAGTGGTAGTGGTAGTGCTAATGTTCCTGCTACTGCTATTC-
HisHisHisHisHisHisAspTyrLysAspAspAspAspLys

TAATGA 3'
ATTACT 5'
StpStp
```

Sf9 insect cells were transfected with pHF/Flt and a virus stock was prepared. After infection of Sf9 cells with recombinant virus, medium was collected. The soluble secreted Flt3-$His_6$-FLAG expression product was purified from the medium using a nickel-NTA resin from Qiagen. The purified Flt3 receptor was coupled to an M2 anti-FLAG antibody column. See below.

Purification of the Flt3 Ligand

The Flt3 ligand was isolated by a combination of affinity chromatography using the Flt3 receptor as a specific binding reagent in combination with the earlier defined physical properties allowing separation from other proteins and contaminants. Similar techniques using human cell assays and human cell sources could be applied to isolate a human ligand.

100 L of crude TA4 supernatant was buffer exchanged into PBS and concentrated to 1000×. This was then tumbled overnight with 2 ml M2 (anti-FLAG) beads that had been preloaded with soluble Flt3. The beads were then washed with several column volumes of PBS, and the bound material was eluted with 3 ml 100 mM glycine, pH 2.5. The eluate was collected into a tube containing sufficient 2 M Tris, pH 7.5 to neutralize the glycine. The neutralized eluate was then loaded onto a 4.6×100 mm Poros R/H column and the proteins chromatographed with a linear water/acetonitrile gradient in 0.1%

TFA. Samples of each fraction were dried down for bioassay and SDS-PAGE. The molecule representing the Flt3 ligand activity ran on reduced SDS-PAGE as an apparently glycosylated protein at approximately 30 kilodaltons. Fractions containing the bulk of the biological activity were dried down completely and combined into sufficient Laemmli gel sample buffer (containing DTT) to be run in a single lane on a 12% mini-gel (SDS-PAGE). The gel was stained with Coomassie blue, destained, and the band representing the Flt3 ligand was carefully excised. This slice contained biochemically pure Flt3 ligand. 100 L of TA4 cell supernatant contained less than 5 micrograms of this protein. The purified protein has a specific activity of $1 \times 10^7$ Units per milligram on the Baf assay. One unit is that which provides half maximum stimulation in a 100 µl assay.

In a second purification, greater than 90% of the Flt3 ligand in 200 L of TA4-conditioned medium was adsorbed with 5 ml of Flt3/Flk2 affinity beads, eluted with 0.1 M glycine, pH 2.5, and chromatographed on a 4.6×200 mm Poros R/H (PerSeptive) reversed phase column with a linear 28% to 40% $CH_3CN$ gradient (into $H_2O$ with 0.1% TFA). Active fractions were combined, dried, dissolved in reduced Laemli sample buffer and electrophoresed in a single lane of an SDS-PAGE mini-gel.

To aid in the identification of the ligand, the two column eluates were separately chromatographed on reverse-phase (RP) HPLC, and the fractions assayed for biological activity and analyzed by SDS-PAGE. The eluate from the primary depletion produced a large peak of Flt3 ligand activity, highest in fractions 56-58, while the eluate from the secondary depletion showed very little activity at the equivalent position. SDS-PAGE analysis of samples from each of the fractions from the primary depletion revealed a prominent band at approximately 30 kD whose elution pattern precisely coincided with the peak of biological activity. Similar analyses of samples from the secondary depletion showed only a trace of this species with a minimal level of activity, while the other bands, presumably contaminants, were present at comparable levels in both gels. This data identified the naturally occurring soluble Flt3 ligand as an approximately 30 kD polypeptide, and showed that a combination of affinity chromatography, RP-HPLC, and SDS-PAGE purified the molecule to near homogeneity. Other experiments demonstrated that the native ligand is a non-disulfide linked homodimer with an approximate molecular weight of 65 kD. Under the conditions of our bioassay, highly purified Flt3 ligand (>300,000-fold) has a specific activity of $3.0 \times 10^6$ units/mg. Like the crude activity, purified ligand can induce tyrosine autophosphorylation of Flt3/Flk2 receptor on Baflt cells.

Generation and Purification of Tryptic Peptides of Flt3 Ligand

Flt3 ligand isolated by preparative SDS-PAGE was either transferred onto a membrane for direct sequencing of the amino terminus or digested with proteolytic enzymes for sequencing of individual peptides. Forty-two amino terminal residues were deduced from combined direct sequencing and overlapping of internal peptide sequences; in addition two non-contiguous peptide sequences were determined.

The prep gel slice containing ligand was briefly rinsed with water and acetonitrile to remove excess SDS, smashed into tiny fragments, taken to dryness under vacuum on a SpeedVac (Savant), and then solubilized in 0.2 ml Tris buffer (pH 7.5) containing 0.5 µg modified trypsin (a chemically modified form that will not digest itself) plus 2 mM DTT, and 0.01% Tween 20. The cleavage reaction was carried out at 37° C. for 6 hr, at which time a second 0.5 µg aliquot of trypsin was added, and the digestion continued overnight. The reaction mix was spun at 13 K and loaded onto a 2.1×100 mm Aquapore RP-300 reversed phase column, and peptides eluted with a linear 4-44% acetonitrile gradient (with constant 0.1% TFA). In some cases peptides were rechromatographed on the same column with a 16-44% acetonitrile gradient (with constant 0.1 mM heptafluorobutyric acid (HFBA)). Eluting peptides were monitored at both 215 nm and 280 nm and were collected by hand.

Alternatively, a gel purified band of homogeneous Flt3 ligand was then either blotted to PVDF membrane for direct amino-terminal sequencing or excised and digested with endoproteinases (including trypsin, chymotrypsin, or AspN) for sequence determination from peptides purified by microbore RP-HPLC. Sequence information was obtained with Applied Biosystems 476A and 477A gas phase sequencers.

Determination of the Amino Acid Sequence of Peptides of the Flt3 Ligand.

Peptide sequences were determined using an Applied Biosystems 477A Sequencer. Fragments provided peptide sequences of Table 1 reconstructed into consensus sequences; peptide 17 is the amino terminus: (see SEQ ID NO: 38 and 6)

12. FVQTXISHLLK
13. DYPVTVAVNLQ
14. TPDAYFSHSPISSNFKVKFRELTVHLLK
15. WIEQLK
16. ILFXLFAQYR
17. TPDCY FSHSP ISSNF KVKFR ELTVH LLKDY PVTVA VNLQD EK

III. Isolation of a DNA Clone Encoding Flt3 Ligand

The purified protein or defined peptides are useful for generating antibodies by standard methods, as described above. Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. Alternatively, the Flt3 receptor is used as a specific binding reagent, and advantage can be taken of its specificity of binding, much like an antibody would be used. In either case, the binding reagent is either labeled as described above, e.g., fluorescence or otherwise, or immobilized to a substrate for panning methods.

The binding composition is used for screening of an expression library made from a cell line which expresses a Flt3 ligand. Standard staining techniques are used to detect or sort intracellular or surface expressed ligand, or surface expressing transformed cells are screened by panning. Screening of intracellular expression is performed by various staining or immunofluorescence procedures. See also McMahan, et al. (1991) *EMBO J.* 10:2821-2832.

For example, on day 0, precoat 2-chamber permanox slides with 1 ml per chamber of fibronectin, 10 ng/ml in PBS, for 30 min at room temperature. Rinse once with PBS. Then plate COS cells at $2-3 \times 10^5$ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of huIL-10-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min.

Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 µl/ml of 1M $NaN_3$ for 20 min. Cells are then washed with HBSS/saponin 1×. Soluble Flt3 receptor/antibody complex to cells and incubate for 30 min. Wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85-90° C.

Alternatively, the binding compositions are used to affinity purify or sort out cells expressing the ligand. See, e.g., Sambrook, et al. or Ausubel et al.

In another method, the peptide segments are used to predict appropriate oligonucleotides to screen a library. The genetic code is used to select appropriate oligonucleotides useful as probes for screening a library. See, e.g., Table 3. In combination with polymerase chain reaction (PCR) techniques, synthetic oligonucleotides in appropriate orientations are used as primers to select correct clones from a library. Various combinations of upstream/downstream sense/antisense combinations are tested until an appropriate clone is amplified and detected.

cDNAs encoding the mature end of the mouse FL were isolated in two rounds of PCR using degenerate oligonucleotides based on amino-terminal amino acid sequence. The first round was performed using plasmid DNA from a TA4 cDNA library as a template with a 5' vector-derived primer and a 3' degenerate primer encoding the peptide NLQDEK. A second round of PCR was performed using a 5' degenerate primer encoding the peptide TPDCYF and a 3' degenerate primer encoding the peptide YPVTVA and 10% of the product from the first round as template. A 105 bp PCR product was identified by DNA blot analysis using a radiolabelled internal degenerate oligonucleotide encoding the peptide, NFKVKF. This PCR product, when isolated and sequenced, was shown to encode the expected 35 amino acid peptide. A 303 bp fragment was generated using PCR with a primer corresponding to the 5' end of the 105 bp fragment and a 3' degenerate primer encoding the peptide FVQTNI. This fragment was used to screen $10^6$ plaques of a TA4 cDNA library in λZap II (Stratagene). T118 and T110, two positive clones containing inserts of ~1.6 and ~1.4 kb respectively, were isolated.

The first 163 codons of the T118 and T110 open reading frames are identical; these sequences then diverge at codon 164, presumably due to alternative splicing, to encode two distinct carboxy termini. The 273 residue polypeptide encoded by clone T110 is the longer of the two and contains a putative transmembrane segment comprised of 22 hydrophobic amino acids followed by a cytoplasmic tail. Clone T118 encodes a 220 residue polypeptide with a hydrophobic carboxy terminus suggesting that it also may be primarily membrane associated. Both cDNAs encode identical 27 residue amino terminal signal peptides.

Figure 2:
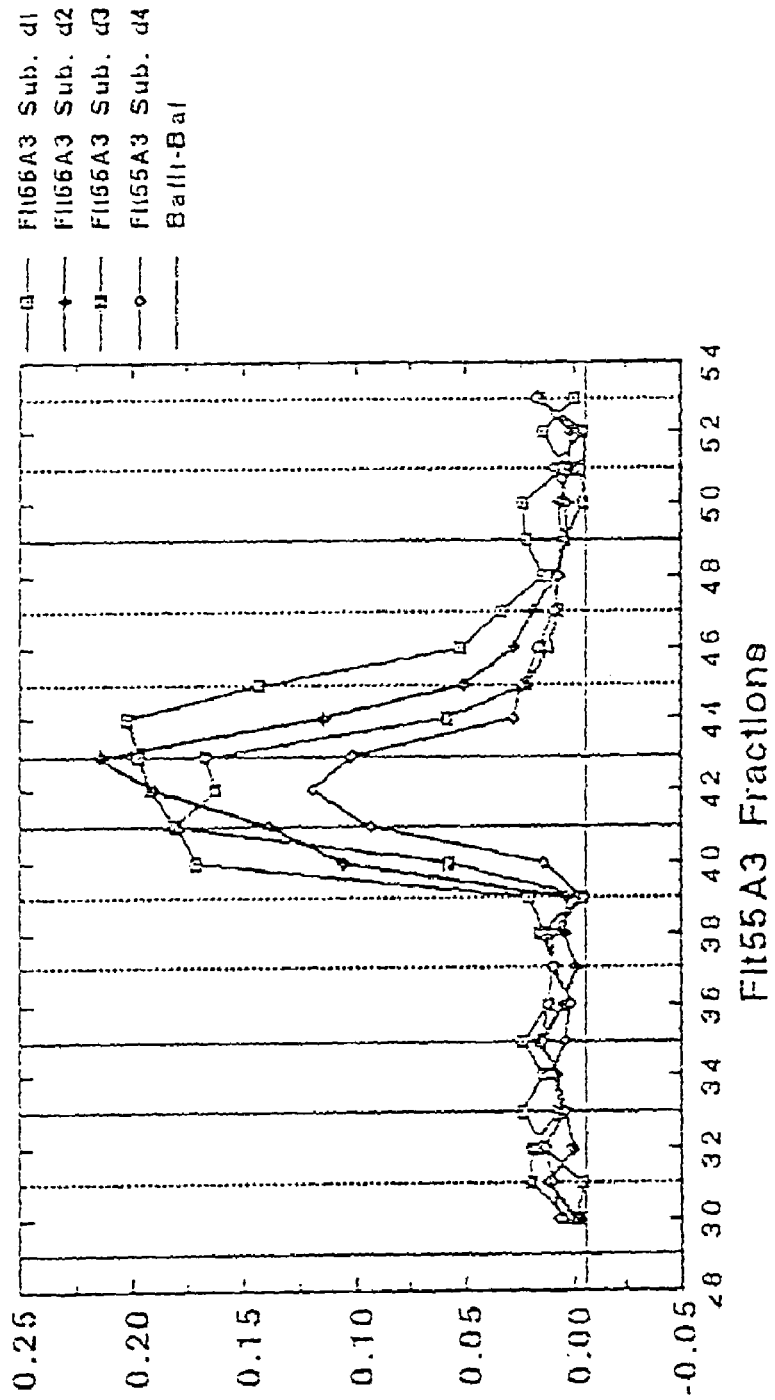
FIG. 2 shows the activity profile of a preparation of purified Flt3 ligand from reverse phase chromatography.
Figure 3:
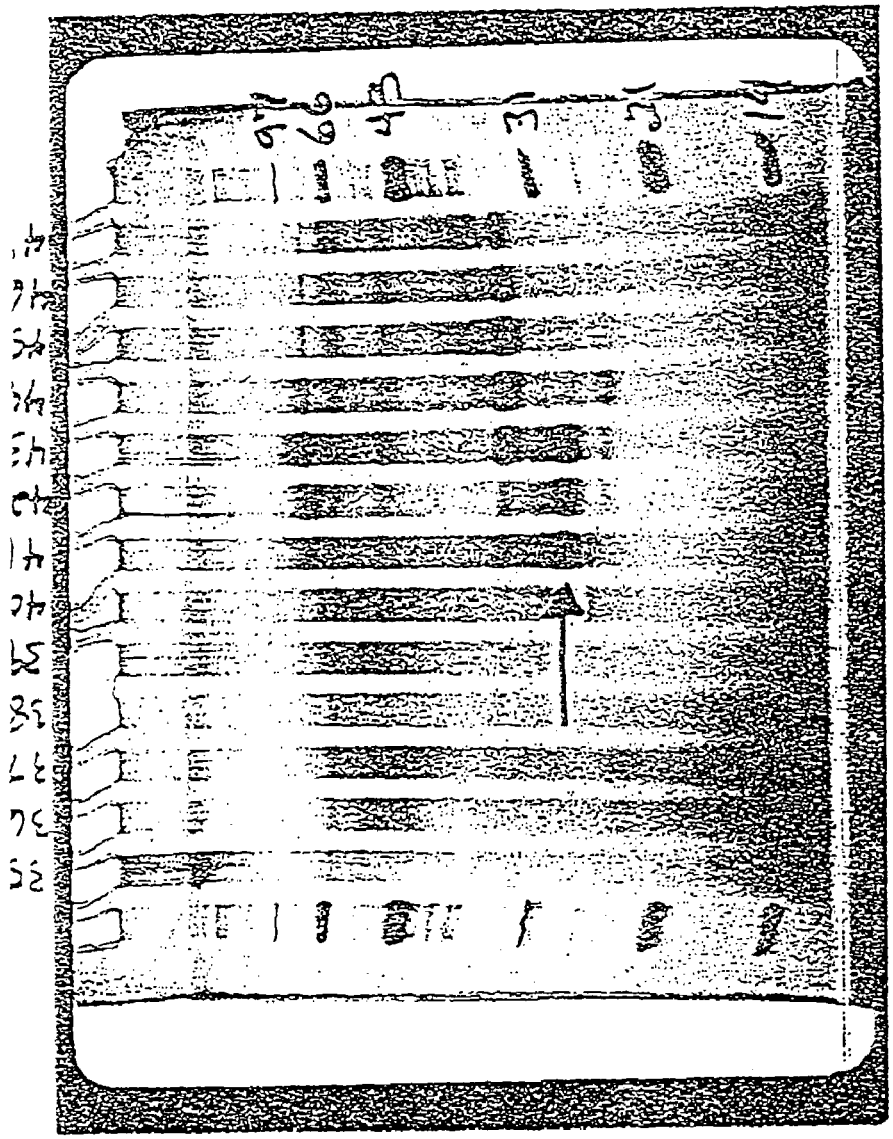
FIG. 3 shows an SDS-PAGE gel profile of a preparation of purified Flt3 ligand from reverse phase chromatography.

Human Flt3 ligand cDNAs were isolated by hybridization with mouse Flt3 ligand cDNA probes using a cDNA library from a human thymic stromal cell (SV48) shown to produce Flt3 ligand activity. See below. Two clones, S86 and S109, have identical open reading frames for the first 160 codons except for a 28 bp insertion in S109; they diverge at the same position as the mouse clones to encode distinct carboxy termini (FIG. 2b). Clone S86 encodes a polypeptide of 235 amino acids which is homologous to mouse clone T110 (66% identical) including a similar transmembrane segment. Clone S109 contains an in frame stop codon in the 28 bp insert which likely represents an exon resulting from aberrant splicing. Excluding this putative exon, clone S109 encodes a 245 amino acid polypeptide containing a distinct, predominantly hydrophilic, carboxy terminus which probably corresponds to a soluble form of the ligand.

All cDNA inserts were subcloned into M13mp18 and 19 for sequencing of both strands using the chain termination method. The nucleic acid sequences have been deposited in GenBank with the accession numbers U04806 and U04807.

The various mouse and human cDNAs define a family of Flt3 ligand molecules sharing a common amino terminus encompassing approximately 135 amino acid residues (including the signal peptide). Comparative sequence analysis suggests that this portion of Flt3 ligand is structurally related to kit ligand and M-CSF, which adopt the α-helical cytokine fold, see Bazan (1991) *Cell* 65:9-10; Pandit, et al. (1992) *Science* 258:1358-1362; and Sprang, et al. (1993) *Curr. Opin. Strucr. Biol.* 3:815-827. In particular, Flt3 ligand is predicted to share the disulfide bridge network of Kit ligand and M-CSF. The divergence point of the mouse and human Flt3 ligand cDNAs occurs at a position analogous to the chain-length variable region of Kit ligand and M-CSF that is thought to tether the receptor-binding cytokine domains of these molecules to the membrane.

Alternatively, a functional screening approach is applied based upon a biological assay for the ligand. The Baf pro-B cell line is transfected with the receptor cDNA to generate a stable transfectant. The transfectant exhibits a mitogenic response to the TA4 stromal cell supernatants, especially detectable when the supernatant is concentrated 100×. The parental transfectant cells are non-responsive to the supernatants. An expression cDNA library made from the producing TA4 cells is made. Pools of random cDNA clones are transfected into COS monkey cells and supernatants are screened for ligand biological activity. Positive pools are subdivided to isolate single clones.

In another approach, expression screening is based upon a biochemical assay for a soluble ligand. The assay is based upon the autophosphorylation activity rather than the mitogenic activity. Total cell lysates of the exposed test cells are prepared and immunoprecipitated with anti-phosphotyrosine antiserum. The immunoprecipitate is run on a polyacrylamide gel, and is, e.g., blotted to a filter and developed with antibody staining of phosphotyrosine.

In yet another approach, functional screening of a membrane bound ligand is by either mitogenic bioassay or biochemical autophosphorylation assay. Appropriate fusion vectors can produce an appropriate expression construct.

Another strategy is to screen for a membrane bound ligand by panning. The receptor cDNA is constructed as described above. The soluble receptor or antibodies raised against the defined peptide fragments can be immobilized and used to immobilize expressing cells. Immobilization may be achieved by use of appropriate antibodies which recognize, e.g., the FLAG sequence of the soluble receptor construct, or by use of antibodies raised against the first antibodies. Recursive cycles of selection and amplification lead to enrichment of appropriate clones and eventual isolation of ligand expressing clones.

Phage expression libraries can be screened by soluble receptor or anti-fragment antibodies. Appropriate label techniques, e.g., anti-FLAG antibodies, will allow specific labeling of appropriate clones.

Screening by hybridization using degenerate probes based upon the peptide sequences will also allow isolation of appropriate clones. Alternatively, use of appropriate primers for PCR screening will yield enrichment of appropriate nucleic acid clones.

Similar methods are applicable to isolate either species or allelic variants. Species variants are isolated using cross-species hybridization techniques based upon isolation of a full length isolate or fragment from one species as a probe. Alternatively, similar assays can be developed, e.g., in human cells for isolation of the Flt3 ligand activity. The mouse cell assays detect a human Flt3 ligand activity, e.g., in human thymic epithelial SV48 cells.

PCR amplification using degenerate primers based upon vector and downstream sequences generated products in a first round of PCR amplification. Primers based upon a vector sequence and degenerate primers from the NLQDEK peptide sequence were used in the first round of amplification. The product of the first amplification was subjected to a second round of PCR amplification using degenerate primers based upon TPDCYF and YPVTVAV peptide sequences. The product of this second round of PCR amplification resulted in a 108 bp product probed using probes based upon NFKVKF sequence. The length is consistent with that predicted by the provided sequence. Sequencing of this 108 bp product provided the nucleotide sequence ACT CCT GAC TGT TAC TTC AGC CAC AGT CCC ATC TCC TCC AAC TTC AAA GTG AAG TTT AGA GAG TTG ACT GAC CAC CTG CTT AAA GAT, which encodes the expected peptide sequence. Further sequencing of a clone has provided the sequence of Table 5.

TABLE 5 nucleotide sequence (5' to 3') from a Flt3 ligand fragment clone and the corresponding amino acid sequence (amino to carboxy). See SEQ ID NO: 37-38.

ACTCCTGACTGTTACTTCAGCCACAGTCCCATCTCCTCCAACTTCAAAGTG
THRPROASPCYSTYRPHESERHISSERPROILESERSERASNPHELYSVAL

AAGTTTAGAGAGTTGACTGACCACCTGCTTAAAGATTACCCAGTCACTGTG
LYSPHEARGGLULEUTHRASPHISLEULEULYSSAPTYRPROVALTHRVAL

GCCGTCAATCTTCAGGACGAGAAGCACTGCAAGGCCTTGTGGAGCCTCTTC
ALAVALASNLEUGLNASPGLULYSHISCYSLYSALALEUTRPSERLEUPHE

CTAGCCCAGCGCTGGATAGAGCAACTGAAGACTGTGGCAGGGTCTAAGATG
LEUALAGLNARGTRPILEGLUGLNLEULYSTHRVALALAGLYSERLYSMET

CAAACGCTTCTGGAGGACGTCAACACCGAGATACATTTTGTCACCTCATGT
GLNTHRLEULEUGLUASPVALASNTHRGLUILEHISPHEVALTHRSERVYS

ACCTTCCAGCCCCTACCAGAATGTCTGCGATTCGTACAGACCAATATA
THRPHEGLNPROLEUPROGLUCYSLEUARGPHEVALGLNTHRASNILE

These sequences eliminate degeneracy of the relevant encoding nucleic acid sequence. This probe is used to screen longer or full length libraries, e.g., from mouse or other mammalian species. Allelic variants and other related genes will also be isolatable using, e.g., hybridization techniques. See Sambrook, et al. and Ausubel, et. al.

IV. Isolation of a DNA Clone Encoding Human Flt3 Ligand

A human 29SV48 stromal cell cDNA library in pME18S, constructed from poly A+ mRNA, was screened with an 800 bp DNA fragment derived from the mouse T118 clone. This fragment encompasses the coding region conserved between the two mouse clones, T118 and T110 (see Table 3). Hybridization of filters with $^{32}$P labeled probe was carried out in a solution of 20% formamide, 6×SSPE, 5×Denhardt's, 100 µg/ml tRNA, and 0.1% SDS at 42° C. overnight. Filters were washed two times at room temperature with 2×SSC and 0.1% SDS for 10-15 minutes. Filters were then washed in 0.1× SSPE, 0.1% SDS under one of the following conditions: three times at 50° C. for 30 min each; three times at 55° C. for 30 min each; once at 55° C. for 30 min and once at 60° C. for 30 min; or once at 60° C. for 30 min.

Approximately 20 positive colonies were selected using these conditions. These were partially sequenced and two clones, S86 and S109 were found to be approximately 75% homologous to the mouse clones over the first 163 amino acids. Clone S86 continued to show homology to clone T110 until the stop codon, although to a lesser degree, for an overall homology of 66%. Clones T118 and S109 do not show homology to each other or the other clones after mouse residue 163 (human residue 160). An additional mouse clone designated MB8 has a 29 amino acid insert at the junction between the common and divergent portions of the mouse ligand.

V. Northern Blot Analysis of Flt3 Ligand mRNA Expression

Examination of both mouse and human Flt3 ligand mRNA in adult and fetal tissues by Northern analysis showed widespread expression, with the highest levels in spleen and lung, with detectable but lower levels in other tissues. The predominant mouse and human transcripts found were approximately 1.5 kb, corresponding in length to these longest cDNA clones, although in mouse at least two longer forms of 3.5 kb and 5.0 kb were also detected. Flt3 ligand mRNAs were found in mouse and human stromal lines, but the highest levels were in T cell lines and peripheral blood mononuclear cells. Although high mRNA levels were found in many T cell lines, in one case these levels are not inducible with ConA and recovery of a soluble biologically active protein from T cell conditioned medium has not yet been achieved.

VI. Alternative Message Forms

Mouse clone T110 and its human counterpart S86, when transiently transfected into COS cells, produce soluble activities which induce proliferation of Baflt cells but not Ba/F3 cells. When the chain terminating exon in S109 is removed, it too can direct the synthesis of soluble ligand activity in COS cells. It would seem that the soluble activity produced by clones T110 and S86 must require some proteolytic processing due to the presence of transmembrane segments, but at present the site of processing is unclear. To confirm that the portion of the molecule predicted to have a structure similar to Kit ligand, M-CSF, and other cytokines is functional, an artificial form was engineered which includes only the first 189 residues of clone T110 eliminating the transmembrane and cytoplasmic tail. When this clone, T110S, is transfected into COS cells, it consistently produces the highest levels of soluble Flt3 ligand activity. Mouse clone T118, which encodes a protein with a very hydrophobic tail, expresses the lowest levels of soluble activity in COS cells, detectable only if the conditioned medium is concentrated. All the recombinant forms, both mouse and human, appear to have similar relative levels of activity whether assayed on Ba/F3 cells expressing the mouse or human receptor.

VII. Effects on Bone Marrow Stem Cells

The cDNA inserts from phage clones T110 and T118 were subcloned into pME18S, see McKenzie, et al. (1993) *Proc. Nat'l Acad. Sci. USA* 90:3735-3739; clones S86 and S109 were isolated in the same vector. Supernatants from the transiently expressing cells were collected 72 hours after transfection and assayed on Baflt cells. Procedures for sorting Thy$^{lo}$ Sca-1$^+$ Lin$^-$ cells, Spangrude, et al. (1988) *Science* 241:58-62, and colony-forming assays, Heimfeld, et al. (1991) *Proc. Nat'l Acad. Sci. USA* 88:9902-9906, have been described. Growth factors were used at concentrations previously stated (Heimfeld, et al. (1991)) except for recombinant mouse Kit ligand (R&D Labs, 20 ng/ml) and purified native mouse Flt3 ligand (25 U/ml). Cultures were scored at day 7. Balb/C day 14 fetal thymocytes were cultured for 72 h with appropriate recombinant cytokines. mIL-12 was used at 1000 U/ml, mKit ligand at 20 U/ml, and recombinant hFlt3 ligand at 100 U/ml. Cell proliferation was measured by the incorporation of $^3$H-thymidine.

When purified native mouse Flt3 ligand was added alone to this cell population, no induction of colony growth was detected. However, when Flt3 ligand was combined with the multilineage growth factor IL-3, colony numbers were approximately double those in the presence of IL-3 alone. These conditions produced multilineage colonies, but they did not contain the abundant erythroid cells found with Kit ligand and IL-3. A similar enhancement of colony numbers is observed when Flt3 ligand is added to IL-6.

Lineage Depleted Bone Marrow Cells.

(Lin$^-$ BM) BM cells were overlaid on Lymphopaque (Accurate Chem., Westbury, N.Y.) and centrifuged at 400×g for 20 min. Cells were removed from the interface, washed, and then incubated with unmodified rat monoclonal antibodies specific for CD2 (RM2.2; see Yagata, et al. (1989) *Proc. Nat'l Acad. Sci. USA* 86:645-649), CD8 (53.6.7; see Ledbetter, et al. *Immunol. Rev.* 47:63-90), B220 (RA3-6B2; see Coffman, et al. (1981) *Nature* 289:681-683), Mac1 (M1/70; see Springer, et al. (1979) *Eur. J. Immunol.* 9:301-306), GR1 (RB6-8C5; see Julia, et al. (1988) *Eur. J. Immunol.* 19:1819-1826), and erythrocytes (Ter-119; see Spangrude, et al. (1990) *Exp. Hemat.* 18:920-926). Lineage positive cells were depleted using magnetic particles coated with Goat anti-rat antibodies (Advanced Magnetics, Cambridge, Mass.) in two successive rounds of treatment.

Hematopoietic Colony Forming Assays.

5×10$^3$ Lin$^-$ BM cells were seeded in 35 mm culture dishes (Falcon, Lincoln Park, N.J.) containing 1 ml modified Iscove's Medium (JRH, Kansas City Kans.), 20% fetal calf serum (FCS) (JRH), 50 mM 2-mercaptoethanol, and 0.8% (wt/vol) methylcellulose. All cultures were supplemented with saturating concentrations of Flt3 ligand, various growth factors, or a combination of these. Plates were incubated at 37° C. in a humidified atmosphere flushed with 5% CO$_2$. After 6, 7, or 26 days of culture the number and size of colonies were analyzed. Cell morphologies were determined after sequentially picked colonies were applied to glass slides and stained with Wright-Giemsa. See Table 6.

TABLE 6

Effect of Flt3 ligand on bone marrow colonies.

| FACTORS | COLONIES per 10$^5$ cells | COLONIES >0.5 mm per 10$^5$ cells | Cells/colony (×10$^3$) |
| --- | --- | --- | --- |
| FL | 5.56 ± 4.19 | 0.67 ± 1.21 | 1875 |
| G-CSF | 70.67 ± 39.21 | 0 | 525 |
| FL + G-CSF | 156 ± 71.91 | 40.5 ± 7.74 | 27,900 |
| IL-6 | 23.33 ± 11.29 | 0 | 675 |
| FL + IL-6 | 82.5 ± 19.95 | 44.29 ± 17.52 | 27,150 |
| M-CSF | 131.85 ± 9.99 | 0 | 975 |
| FL + M-CSF | 141 ± 22.87 | 1.5 ± 0.5 | 1470 |

FL = Flt3 ligand

VIII. Effects on Human Fetal Liver Progenitor Cells

Light density human fetal liver cells were depleted of glycophorin+ cells, see Bárcena, et al. (1993) *Blood* 82:3401-3414. Progenitors were sorted from glycophorin-fetal liver cells based on the lack of staining with PE-labeled CD3, CD14, CD16, CD20, and CD56 (Lin$^-$) (Becton-Dickinson) and positive staining with FITC-labeled CD34 (HPCA-2, Becton-Dickinson) and TC-labeled CD33 (Caltag Labs). CD34+ CD33+ Lin$^-$ cells were cultured in the presence of combinations of recombinant hGM-CSF (Schering-Plough, 10 ng/ml), recombinant hIL-3 (R&D Labs, 20 ng/ml), native mFlt3 ligand (25 U/ml), and recombinant hKL (R&D Labs, 20 ng/ml) for 21 days in agarose cultures, as described by Bárcena, et al. (1993). Cultures were scored for LPP-CFC (colonies >50 cells) and HPP-CFC (colonies >0.5 mm in diameter). Glycophorin-human fetal liver cells were cultured in the presence of combinations of recombinant hEPO (R&D Labs, 1 U/ml), purified native mFlt3 ligand and recombinant human Kit ligand for 14 days in 1.2% methylcellulose cultures, see Heimfeld, et al. (1991).

When CD34+ CD33+ Lin$^-$ human fetal liver progenitor cells were used, purified native Flt3 ligand alone had little or no stimulatory activity. However, as with mouse stem cells, it had a synergistic effect in combination with IL-3 as well as with GM-CSF. In this case, the co-stimulatory effects of Flt3 ligand were observed on both low proliferative potential colony-forming cells (LPP-CFC) as well as the more primitive high proliferative potential colony-forming cells (HPP-CFC). Identical results were obtained when purified recombinant human Flt3 ligand was used in combination with GM-CSF in similar experiments. Consistent with the results obtained with mouse stem cells, Flt3 ligand did not detectably augment the growth of human fetal liver burst-forming units erythroid (BFU-E) in the presence of erythropoietin. Taken together these results indicate that Flt3 ligand enhances the response of stem and primitive progenitor cells to other growth factors to generate all myeloid lineages with the exception of erythroid cells.

Because of the presence of Flt3/Flk2 on immature lymphoid cells as well as myeloid cells, the response of thymocytes to purified Flt3 ligand was examined. In a previous study mouse adult pre-T cells were observed to proliferate in response to IL-12 and Kit ligand. IL-12 in combination with Flt3 ligand or Kit ligand induced significant proliferation in day 14 mouse fetal thymocytes, a cell population consisting predominantly of pre-T cells. These results suggest a role for Flt3 ligand in T cell development.

IX. Effects on Human Pro-B Cells in Co-Culture with Murine Bone Marrow Stromal Cells Cytokines and Monoclonal Antibodies (MoAb).

Recombinant human (rh) IL-7, rhKit ligand, and rhIL-3 were purchased from R&D Systems, Inc. (Minneapolis, Minn.). rhGM-CSF and recombinant murine (rm) Flt3 ligand were produced using standard procedures. Kit ligand, GM-CSF, and IL-3 were used at 20 ng/ml and rmFlt3 ligand was used at 50 BaFlt units/ml. Phycoerythrin (PE)-labeled CD19 (Leu12), PE-labeled CD20 (Leu16), and fluorescein isothiocyanate (FITC)-labeled CD34 (HPCA2) were purchased from Becton Dickinson (San Jose, Calif.) and glycophorin A (GPA) antibody (10F7MN) for the depletion of erythroid cells was obtained from American Type Tissue Culture Collection, Rockville, Md.

Isolation of Human Fetal Bone Marrow (BM) Progenitors.

Human fetal BM, of gestational ages ranging from 18 to 24 weeks, were obtained from Advanced Bioscience Resources (Alameda, Calif.) and were used with the approval of the Committee for the Protection of Human Subjects at DNAX. The gestational age of the abortuses was approximated by the crown-rump method. A single tissue was used in each experiment.

Fetal BM cells were prepared for cell sorting by density centrifugation and immunomagnetic bead depletion (Dynal Inc., Great Neck, N.Y.) of grycophorin A (GPA) positive erythroid cells as previously described. See Muench, et al. (1994) *Blood* 83:3170-3181. These GPA⁻ light density fetal BM cells were then stained with PE-labeled CD19 and FITC-labeled CD34. Cell sorting was accomplished by setting an electronic gate on cells with a low side light-scatter and a moderate forward light-scatter.

CD34+CD19+/CD34−CD19+ and CD34+CD19+CD20+/CD20− cell populations were isolated by standard procedures.

Tissue Culture.

A murine BM stromal cell line, 30R, was cultured in RPMI-1640 medium supplemented with 5% FCS (Sigma), $5 \times 10^{-5}$ M 2-mercaptoethanol, and pen-strep (Whitlock-Witte (WW) medium). Proliferation assays and pro-B cell cultures were conducted with WW medium unless otherwise indicated. In some of the experiments, serum-deprived (SD) culture medium consisted of Iscove's modified Dulbecco's medium (IMDM) (Sigma Chemical Company, St. Louis, Mo.) supplemented with $7.5 \times 10^{-5}$ M α-thioglycerol (Sigma Chemical Company), 50 µg/ml gentamicin (Gibco BRL, Grand Island, N.Y.), 2% fraction-V ethanol-extracted bovine serum albumin (BSA) (Boehringer Mannheim Biochemicals, Indianapolis, Ind.), 200 µg/ml human iron-saturated transferrin (Boehringer Mannheim Biochemicals), 10 µg/ml recombinant human insulin (Boehringer Mannheim Biochemicals), and 40 µg protein/ml human low density lipoprotein (Sigma Chemical Company) was used to avoid the potential contamination of cytokines from FCS.

Proliferation Assays.

Murine BM stromal cell line, 30R, was irradiated at 1 Gy and plated in 96-well flat-bottom tissue-culture plates (Becton Dickinson) 1 or 2 days before initiating co-culture. Quadriplicate or triplicate cultures were established with 5000 sorted BM B cells in a volume of total 200 µl medium containing the indicated concentrations of cytokines. The proliferation of B cells in response to cytokines was determined by measuring the incorporation of ³H-thymidine during a 7 hour pulse with 1 µCi at 7-10 days of culture.

Proliferation Kinetics and Phenotypic Analysis of Cultured Pro B Cells.

Sorted pro-B cells were cultured at the concentration of $1.5-2.0 \times 10^4$ cells/ml/well with (20 ng/ml) or without IL-7 on pre-established 30R cultures in 24 well plates. Cells were harvested between 7 to 21 days of culture and the number of viable hematopoietic cell counts were determined by trypan blue dye exclusion. Small round lymphoid cells could be easily discriminated from large stromal cells at 100× light microscope magnification. Increase of cellularity was indicated as relative cell increase by dividing the cell yield with the number of cells inoculated.

The cell surface phenotype of cultured fetal liver cells was determined by two-color flow cytometry using a FACScan (Becton Dickinson). After staining with fluorochrome conjugated antibodies, propidium iodide (PI) was added at a final concentration of 10 µg/ml to gate out dead cells selectively.

Proliferation and Differentiation of CD34+CD19+ Cells in Co-Culture with Murine BM Stromal Cell Line, 30R.

CD34+CD19+ pro-B cells as well as CD34−CD19+ B cells were sorted from low density gradient separated, GPA depleted fetal BM cells. Co-culture of these cells on irradiated 30R with varying doses of exogenous rhIL-7 demonstrated a dose-dependent proliferation of CD34+CD19+ cell population in the proliferation assay. IL-7 was effective at doses over 10 ng/ml, so the dose of 20 ng/ml was selected as a standard condition for the further experiments. Cultures without IL-7, or with low doses of IL-7, did not induce significant proliferation of CD34+CD19+ cells, indicating that this population requires IL-7 for their proliferation. No proliferative signals were obtained from CD34−CD19+ populations at any dose of IL-7 examined.

Proliferation kinetics and differentiation of pro-B cells in this co-culture system were then studied. Cell yield in the co-culture with 20 ng/ml of IL-7 reached a maximum between days 12-18, with a 4-10 fold increase of the cell number. Pro-B cells did not proliferate significantly in the cultures without IL-7, which was concordant with the results obtained by the proliferation assay.

Surface phenotype of the cells growing in the co-culture was analyzed at different time points. At the early periods of culture, such as day 7 or 10, the major population of the cells growing with IL-7 expressed both CD19 and CD20 strongly, and showed a blastoid scatter profile. In contrast, most of those cultured without IL-7 had a small lymphoid profile with negligible expression of CD20. The phenotype of the cells cultured with IL-7, however, changed gradually as time progressed and at the late stage of culture, e.g., later than days 17-18, the phenotypes of the cells with or without IL-7 became similar. The cells cultured with IL-7 predominantly fell in the small lymphoid profile and the expression of CD20 became weaker compared to those examined in the early period of culture. Expression of cytoplasmic IgM chain was examined among the cells proliferated in the co-culture on 30R with IL-7. In all the samples harvested between days 12-21, 30-40% of the cells clearly become positive for cytoplasmic IgM (cµ) staining, whereas only 3-8% of the cells expressed surface IgM (sµ). This demonstrated that the co-culture of human fetal bone marrow pro B cells on xenogeneic murine bone marrow stromal cells supplemented with IL-7 induced proliferation and differentiation of these cells towards cµ positive pre B cell stage.

CD34+CD19+CD20+ Cells are the Major Population to Respond to IL7.

The CD34+CD19+ population is still heterogeneous in terms of the expression of CD20. Therefore, the CD34+

CD19+ pro B cell population was further sorted into CD20+ and CD20– subpopulations and their proliferative potential examined in response to IL-7 in co-culture with BM stromal cells. The CD34+CD19+CD20+ population proliferated as well as the CD34+CD19+ cells whereas the CD34+CD19+ CD20– population did not. These results were confirmed by studying the proliferation kinetics of the two populations. The CD34+CD19+CD20+ population proliferated vigorously by day 14 and then cell yield dropped. The CD34+CD19+ CD20– population also showed a slight increase of cell number at day 14, but the magnitude of increase (2.5 and 3.2 fold increase from two independent experiments) was far lower than the other population (9.3 and 12.5 fold increase). Thus, it was clearly demonstrated that the CD34+CD19+CD20+ population was the major population to proliferate upon the stimulation by IL-7 in the co-culture system. Interestingly, the cells derived from these two populations showed similar phenotypes at each time point analyzed, suggesting that despite the different proliferative potential these two populations possess similar differentiative potentials.

Effects of Various Cytokines on Proliferation of Pro-B Cells.

The effects of other cytokines including IL-3, GM-CSF, Kit ligand, and Flt3 ligand were examined on proliferation of pro B cells, either individually or in combination with IL-7. For the proliferation assay in these experiments, serum depleted (SD) media were used to avoid potential effects by factors derived from fetal calf serum. Experiments were performed also either with irradiated 30R or without stroma cells. IL-7 alone induced the proliferation of pro B cells but no other cytokine examined here gave signals by itself. IL-3 or Flt3 ligand, however, showed clear synergistic effect with IL-7 while no such a effect was seen by GM-CSF or Kit ligand in combination with IL-7. Combination of three factors, IL-3 and Flt3 ligand on top of IL-7, induced the highest proliferation of pro B cells. Concordant results were obtained from 3 experiments with or without stroma j cells. Cell yield of the cultures with various cytokine combinations also correlated well to the results obtained by the proliferation assay. Thus, IL-3 or Flt3 ligand exhibited a synergistic effect with IL-7. The combination of IL-3, Flt3 ligand, and IL-7 reproducibly resulted in the highest cell yield, ranging 150-200% of the cellularity of IL-7 alone between 10-18 days culture.

Presented here is data that a xenogeneic murine bone marrow stromal cell line, 30R, can support the proliferation and differentiation of human fetal BM CD34+CD19+ pro-B cells in vitro in concert with IL-7. Previous studies to establish in vitro cultures of human BM B cell progenitors demonstrated that fetal BM CD10+sµ– B cell progenitors responded to IL-7 in the culture with human bone marrow derived stromal layers. However, most of CD19+ cells in fetal BM co-express a CD10 molecule, and thus, CD10+sµ– fetal BM cells are the mixed populations of CD34+ pro-B cells and CD34– pre-B cells. It is clearly demonstrated here that only the CD34+ pro B cell compartment can proliferate upon IL-7 stimulation. CD34–CD19+ cells and a mixed population of cµ+ pre-B cells, sµ+, and sµ+sδ+ B cells did not proliferate in this system. Pro-B cells, which are negative for cµ expression, can be induced by these cultures to differentiate into cµ+ pre-B cell stage since 30-50% of the cells express cµ after 10-20 days culture. Thus, proliferation and differentiation of human pro-B cells can be induced by IL-7 in the microenvironment reconstituted by a murine BM stromal cell line. The differentiative potential of these pre-B cells generated from pro-B cells in vitro is currently being investigated under the condition in which normal fetal BM pre B cells differentiate into Ig producing cells.

In vitro culture of human hematopoietic progenitor cells on murine bone marrow stromal cells have been reported to maintain early progenitor cell activity. Human B lymphopoiesis can also be supported by murine BM stromal cells, as shown here. These results suggested that human pro-B cells require both BM stromal cells and IL-7, since they did not proliferate effectively with IL-7 without stromal cells, or with stromal cells without exogenously provided IL-7. The ability of various other stromal cell types including thymic epithelial cells, fetal BM fibroblasts, and human VCAM-1 transfected COS cells to support the growth of pro-B cells in conjunction with IL-7 was tested. The fact that none of these stromal cells, except for BM fibroblasts, supported pro-B cell growth effectively suggested the unique role(s) of 30R in supporting human B lymphopoiesis. Studies to identify the role of stromal cells in murine long-term B lymphopoiesis suggested the presence of yet uncloned molecule(s) important for early B cell development other than IL-7 and Kit ligand. Such molecule(s) may be cross-reactive to human pro-B cells. A pre-B cell growth-stimulating factor recently cloned from a murine BM stroma cell line which potentiates the proliferation of mouse pre-B cells upon IL-7 stimulation may be the factor responsible for the stromal cell activity.

Using this xenogeneic co-culture system, the population responding to IL-7 was further characterized. These results demonstrated that among the CD34+ pro-B cell compartment, a CD20+ subpopulation predominantly proliferated upon stimulation given by stromal cells and IL-7. The proliferative potential of CD20+ subpopulation is 5-6 fold higher than that of CD20– subpopulation. Staining of the cultured pro-B cells for CD20 in conjunction with cµ expression revealed that there is no correlation between CD20 expression and cµ expression. Thus, CD20 expression is associated with the proliferative potential but not with cell differentiation stage. CD20 antigen is expressed exclusively on B lineage cells from early stage of differentiation until plasma cell stage. Although the precise function of CD20 molecule is not understood yet, it was reported that CD20 molecule is involved in the activation process required cell cycle progression in mature B cells. These altogether may suggest that the CD20 expression is associated with cell activation status rather than the cell differentiation stage in the early B cell compartment.

Finally, the effects of various cytokines, including recently cloned Flt3 ligand, were tested on human pro-B cell proliferation. Flt3 ligand is a member of the family of tyrosine kinase receptors and shares a structural similarity with the ligands for other members of related receptors, e.g., Kit ligand and M-CSF. Here is reported that Flt3 ligand synergizes with IL-3 and/or GM-CSF on proliferation of early myeloid progenitor cells in fetal liver, though the effect is weaker than Kit ligand. In contrast to a dramatic synergistic effect of Kit ligand on erythropoiesis, Flt3 ligand did not show significant effect on erythropoiesis. This study found that Flt3 ligand has a synergystic effect on pro-B cell proliferation with IL-7, whereas Kit ligand did not show any effect on B lymphopoiesis in combination with IL-7, or IL-7 and stromal cell. Thus, Flt3 ligand and Kit ligand have synergistic effects on different hematopoietic cell lineages, suggesting different roles in regulating hematopoiesis.

In this study, IL-3 also showed a synergistic effect on pro-B cell proliferation with IL-7, which is concordant with the finding that normal and leukemic B precursors express functional IL-3 receptors. It would be of interest to understand the mode of action of IL-3 and Flt3 ligand in synergizing with IL-7. Flt3 ligand is produced in many different organs, including bone marrow, while the expression of receptor is limited in the bone marrow progenitor population. Thus, it is possible that Flt3 ligand plays a regulatory role in BM B lymphopoiesis in a physiological condition. In contrast, IL-3 can be produced only by activated T cells, suggesting that IL-3 augments B lymphopoiesis in pathological conditions, such as acute systemic-infections. These cytokines may be clinically useful to promote the early recovery of B cell compartment after chemotherapy or bone marrow transplantation.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A purified antibody, or binding fragment thereof, wherein the antibody or fragment specifically binds to a Flt3 ligand protein which binds to a Flt3 receptor, wherein said protein has the following physical characteristics:
   a) said protein migrates as an approximately 30 kD glycoprotein on SDS-Polyacrylamide gel electrophoresis under reducing conditions;
   b) said protein precipitates in ammonium sulfate at 60 to 85% saturation at 4° C.;
   c) on hydrophobic interaction chromatography with an $(NH_4)_2SO_4$ gradient in 20 mM Tris, pH 7.5 on a Phenyl-5PW column, said protein elutes between 900-750 mM $(NH_4)_2SO_4$;
   d) on anion exchange chromatography (NaCl gradient in 20 mM Tris, pH 7.5 on Mono Q column), said protein elutes between 130-250 mM NaCl;
   e) on cation exchange chromatography (NaCl gradient in 10 mM citrate, pH 3.0 on Mono S column), said protein elutes between 440-540 mM NaCl;
   f) on gel filtration chromatography (Sephacryl S200 column), said protein runs with an apparent molecular weight of 70 kD;
   g) on reversed phase HPLC (water to acetonitrile gradient in 0.1% TFA on a Poros R/H column), said protein elutes between 32-35% acetonitrile; and
   h) said protein comprises a sequence selected from the group consisting of:
      i) Phe Val Gin Thr Asn Ile Ser His Leu Leu Lys (SEQ. ID No. 1);
      ii) Asp Tyr Pro Val Thr Val Ala Val Xaa Leu Gin Asp Glu (Residues 1-13 of SEQ. ID No. 2); and,
      iii) Trp Ile Glu Gln Leu Lys (Residues 1-6 of SEQ. ID No. 4).

2. The antibody or fragment of claim 1, wherein the antibody is a monoclonal antibody.

3. The antibody or fragment of claim 1, wherein the antibody or fragment is detectably labeled.

4. The antibody or fragment of claim 1, wherein the antibody or fragment blocks binding of Flt3 ligand to the Flt3 receptor.

5. The antibody or fragment of claim 1, wherein the antibody or fragment binds to native Flt3 ligand.

6. A cell producing a monoclonal antibody of claim 2.

7. A kit comprising a first compartment that contains an antibody or binding fragment of claim 1, and a second compartment that contains:
   (a) a purified Flt3 ligand protein; or,
   (b) a secondary antibody that binds the antibody or binding fragment of claim 1.

8. A purified antibody, or binding fragment thereof, wherein the antibody or fragment specifically binds to a Flt3 ligand protein which binds to a Flt3 receptor, wherein said protein has the following physical characteristics:
   a) said protein migrates as an approximately 30 kD glycoprotein on SDS-Polyacrylamide gel electrophoresis under reducing conditions;
   b) on anion exchange chromatography (NaCl gradient in 20 mM Tris, pH 7.5 on Mono Q column), said protein elutes between 130-250 mM NaCl;
   c) on cation exchange chromatography (NaCl gradient in 10 mM citrate, pH 3.0 on Mono S column), said protein elutes between 440-540 mM NaCl; and,
   d) said protein comprises a sequence selected from the group consisting of:
      i) Phe Val Gln Thr Asn Ile Ser His Leu Leu Lys (SEQ. ID No. 1);
      ii) Asp Tyr Pro Val Thr Val Ala Val Xaa Leu Gln Asp Glu (Residues 1-13 of SEQ. ID No. 2); and,
      ii) Trp Ile Glu Gln Leu Lys (Residues 1-6 of SEQ. ID No. 4).

9. The antibody or fragment of claim 8, wherein the antibody is a monoclonal antibody.

10. The antibody or fragment of claim 8, wherein the antibody or fragment is detectably labeled.

11. The antibody or fragment of claim 8, wherein the antibody or fragment blocks binding of Flt3 ligand to the Flt3 receptor.

12. The antibody or fragment of claim 8, wherein the antibody or fragment binds to native Flt3 ligand.

13. A cell producing a monoclonal antibody of claim 9.

14. A kit comprising a first compartment that contains an antibody or binding fragment of claim 8, and a second compartment that contains:
   (a) a purified Flt3 ligand protein; or,
   (b) a secondary antibody that binds the antibody or binding fragment of claim 8.

15. A purified antibody, or binding fragment thereof, wherein the antibody or fragment specifically binds to a Flt3 ligand protein which binds to a Flt3 receptor, wherein said protein has the following physical characteristics:
   a) said protein migrates as an approximately 30 kD glycoprotein on SDS-Polyacrylamide gel electrophoresis under reducing conditions; and,
   b) said protein precipitates in ammonium sulfate at 60 to 85% saturation at 4° C.; and,
   c) said protein comprises a sequence selected from the group consisting of:
      i) Phe Val Gln Thr Asn Ile Ser His Leu Leu Lys (SEQ. ID No. 1);
      ii) Asp Tyr Pro Val Thr Val Ala Val Xaa Leu Gln Asp Glu (Residues 1-13 of SEQ. ID No. 2); and,
      iii) Trp Ile Glu Gln Leu Lys (Residues 1-6 of SEQ. ID No. 4).

16. The antibody or fragment of claim 15, wherein the antibody is a monoclonal antibody.

17. The antibody or fragment of claim 15, wherein the antibody or fragment is detectably labeled.

18. The antibody or fragment of claim 15, wherein the antibody or fragment blocks binding of Flt3 ligand to the Flt3 receptor.

19. The antibody or fragment of claim 15, wherein the antibody or fragment binds to native Flt3 ligand.

20. A cell producing a monoclonal antibody of claim 16.

21. A kit comprising a first compartment that contains an antibody or binding fragment of claim 15, and a second compartment that contains:
   (a) a purified Flt3 ligand protein; or,
   (b) a secondary antibody that binds the antibody or binding fragment of claim 15.

* * * * *